(12) United States Patent
Manting et al.

(10) Patent No.: US 12,364,758 B2
(45) Date of Patent: Jul. 22, 2025

(54) USE OF LEUKEMIA-DERIVED CELLS IN OVARIAN CANCER VACCINES

(71) Applicant: MENDUS B.V., Leiden (NL)

(72) Inventors: Erik Hans Manting, Leiden (NL);
Satwinder Kaur Singh, Leiden (NL);
Jeroen Rovers, Leiden (NL)

(73) Assignee: MENDUS B.V., Leiden (NL)

( * ) Notice: Subject to any disclaimer, the term of this patent is extended or adjusted under 35 U.S.C. 154(b) by 507 days.

(21) Appl. No.: 17/361,477

(22) Filed: Jun. 29, 2021

(65) Prior Publication Data

US 2022/0023405 A1    Jan. 27, 2022

Related U.S. Application Data

(60) Provisional application No. 63/111,390, filed on Nov. 9, 2020, provisional application No. 63/046,520, filed on Jun. 30, 2020.

(51) Int. Cl.
| | | |
|---|---|---|
| A61K 39/00 | (2006.01) | |
| A61K 40/19 | (2025.01) | |
| A61K 40/24 | (2025.01) | |
| A61K 40/42 | (2025.01) | |
| A61P 35/00 | (2006.01) | |
| A61K 40/50 | (2025.01) | |

(52) U.S. Cl.
CPC .......... *A61K 40/4257* (2025.01); *A61K 40/19* (2025.01); *A61K 40/24* (2025.01); *A61K 40/424* (2025.01); *A61K 40/4243* (2025.01); *A61K 40/427* (2025.01); *A61P 35/00* (2018.01); *A61K 2039/545* (2013.01); *A61K 2039/55* (2013.01); *A61K 2039/585* (2013.01); *A61K 2039/892* (2018.08); *A61K 40/50* (2025.01); *A61K 2239/31* (2023.05); *A61K 2239/38* (2023.05); *A61K 2239/59* (2023.05)

(58) Field of Classification Search
CPC ........ A61K 35/13; A61K 40/19; A61K 40/24; A61K 40/50; A61K 2039/585; A61K 2039/892; A61K 2239/59; A61P 35/00
See application file for complete search history.

(56) References Cited

U.S. PATENT DOCUMENTS

| | | |
|---|---|---|
| 4,690,915 A | 9/1987 | Rosenberg |
| 4,797,368 A | 1/1989 | Carter et al. |
| 4,956,778 A | 9/1990 | Naito |
| 5,091,513 A | 2/1992 | Huston et al. |
| 5,132,405 A | 7/1992 | Huston et al. |
| 5,139,941 A | 8/1992 | Muzyczka et al. |
| 5,858,358 A | 1/1999 | June et al. |
| 5,876,989 A | 3/1999 | Berg et al. |
| 5,883,223 A | 3/1999 | Gray |
| 5,993,434 A | 11/1999 | Dev et al. |
| 5,994,136 A | 11/1999 | Naldini et al. |
| 6,013,516 A | 1/2000 | Verma et al. |
| 6,054,297 A | 4/2000 | Carter et al. |
| 6,080,840 A | 6/2000 | Slanetz et al. |
| 6,181,964 B1 | 1/2001 | Hofmann et al. |
| 6,207,156 B1 | 3/2001 | Kuchroo et al. |
| 6,233,482 B1 | 5/2001 | Hofmann et al. |
| 6,516,223 B2 | 2/2003 | Hofmann |
| 6,534,055 B1 | 3/2003 | June et al. |
| 6,567,694 B2 | 5/2003 | Hayakawa |
| 6,582,959 B2 | 6/2003 | Kim |
| 6,678,556 B1 | 1/2004 | Nolan et al. |
| 6,680,301 B2 | 1/2004 | Berg et al. |
| 6,692,964 B1 | 2/2004 | June et al. |
| 6,703,020 B1 | 3/2004 | Thorpe et al. |
| 6,797,514 B2 | 9/2004 | Berenson et al. |
| 6,867,041 B2 | 3/2005 | Berenson et al. |
| 6,884,879 B1 | 4/2005 | Baca et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,060,269 B1 | 6/2006 | Baca et al. |
| 7,067,318 B2 | 6/2006 | June et al. |
| 7,144,575 B2 | 12/2006 | June et al. |
| 7,171,264 B1 | 1/2007 | Hofmann et al. |
| 7,172,869 B2 | 2/2007 | June et al. |
| 7,173,116 B2 | 2/2007 | Fewell et al. |
| 7,175,843 B2 | 2/2007 | June et al. |
| 7,232,566 B2 | 6/2007 | June et al. |
| 7,569,664 B2 | 8/2009 | Jakobsen et al. |
| 7,700,546 B2 | 4/2010 | Mekada et al. |
| 7,754,482 B2 | 7/2010 | Riley et al. |

(Continued)

FOREIGN PATENT DOCUMENTS

| | | |
|---|---|---|
| CA | 3104833 A1 | 1/2020 |
| EP | 0666868 B1 | 4/2002 |

(Continued)

OTHER PUBLICATIONS

Koeffler et al. (Blood. Oct. 1983; 62 (4): 709-21).*
Nagasawa et al. (J. Immunother. Nov. 2020; 8 (Suppl. 3): A102-A103; Abstract 171; pp. 1-2).*
Zuo et al. (Cells. Nov. 19, 2021; 10 (11): 3233; pp. 1-21).*
Da Costa Miranda et al. (Gynecol. Oncol. Feb. 2014; 132 (2): 287-91).*
Bamias et al. (BMC Cancer. Sep. 25, 2006: 6: 228; pp. 1-8).*
Van de Loosdrecht et al. (Cancer Immunol. Immunother. 2018; 67 (10): 1505-18).*
Leaf et al. (J. Immunother. Nov./Dec. 2017 40 (9): 315-22).*

(Continued)

*Primary Examiner* — Hong Sang
(74) *Attorney, Agent, or Firm* — LATHROP GPM LLP; James H. Velema, Esq.; Judith L. Stone-Hulslander, Esq.

(57) ABSTRACT

The present disclosure provides methods for treating a progressive ovarian cancer using an allogeneic leukemia-derived cell. Also provided are immunogenic compositions comprising an allogeneic leukemia-derived cell, and pharmaceutical compositions and formulations thereof.

13 Claims, 6 Drawing Sheets

(56) References Cited

U.S. PATENT DOCUMENTS

| | | |
|---|---|---|
| 8,008,449 B2 | 8/2011 | Korman et al. |
| 8,017,114 B2 | 9/2011 | Korman et al. |
| 8,066,989 B2 | 11/2011 | Lindhofer et al. |
| 8,119,129 B2 | 2/2012 | Jure-Kunkel et al. |
| 8,354,509 B2 | 1/2013 | Carven et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,470,789 B2 | 6/2013 | Van Wetering et al. |
| 8,507,443 B2 | 8/2013 | Mekada et al. |
| 8,586,363 B2 | 11/2013 | Voytas et al. |
| 8,697,853 B2 | 4/2014 | Voytas et al. |
| 8,722,400 B2 | 5/2014 | Riley et al. |
| 8,735,553 B1 | 5/2014 | Li et al. |
| 8,771,985 B2 | 7/2014 | Cui et al. |
| 9,187,758 B2 | 11/2015 | Cai et al. |
| 9,206,404 B2 | 12/2015 | Cui et al. |
| 9,393,257 B2 | 7/2016 | Osborn et al. |
| 9,555,105 B2 | 1/2017 | Riley et al. |
| 9,855,298 B2 | 1/2018 | Bot et al. |
| 9,861,689 B2 | 1/2018 | Mach et al. |
| 10,064,923 B2 * | 9/2018 | Van Wetering ........ A61K 40/24 |
| 10,513,686 B2 | 12/2019 | Ostertag et al. |
| 11,027,001 B2 | 6/2021 | Van Wetering et al. |
| 11,052,144 B2 | 7/2021 | Van Wetering et al. |
| 11,071,778 B2 | 7/2021 | Van Wetering et al. |
| 2003/0170238 A1 | 9/2003 | Gruenberg et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0014645 A1 | 1/2004 | Draghia-Akli et al. |
| 2004/0057935 A1 | 3/2004 | Yu et al. |
| 2004/0059285 A1 | 3/2004 | Mathiesen et al. |
| 2004/0092907 A1 | 5/2004 | Mathiesen et al. |
| 2004/0265998 A1 | 12/2004 | Goeltz et al. |
| 2005/0052630 A1 | 3/2005 | Smith et al. |
| 2005/0070841 A1 | 3/2005 | Mathiesen et al. |
| 2005/0075308 A1 | 4/2005 | Wilson et al. |
| 2005/0112126 A1 | 5/2005 | Baca et al. |
| 2005/0186208 A1 | 8/2005 | Fyfe et al. |
| 2005/0196754 A1 | 9/2005 | Drmanac et al. |
| 2006/0002899 A1 | 1/2006 | Rice et al. |
| 2006/0009360 A1 | 1/2006 | Pifer et al. |
| 2006/0121005 A1 | 6/2006 | Berenson et al. |
| 2007/0041954 A1 | 2/2007 | Ichim |
| 2007/0128708 A1 | 6/2007 | Gamelin |
| 2011/0117051 A1 | 5/2011 | Van Wetering et al. |
| 2012/0294796 A1 | 11/2012 | Johnson et al. |
| 2013/0274134 A1 | 10/2013 | Lindstedt et al. |
| 2013/0330399 A1 | 12/2013 | Reisfeld et al. |
| 2015/0166955 A1 | 6/2015 | Van Wetering et al. |
| 2015/0297698 A1 | 10/2015 | Van Wetering et al. |
| 2018/0002397 A1 | 1/2018 | Shah et al. |
| 2018/0236054 A1 | 8/2018 | Sampson et al. |
| 2018/0346541 A1 | 12/2018 | Wong et al. |
| 2019/0000945 A1 | 1/2019 | Van Wetering et al. |
| 2019/0055297 A1 | 2/2019 | Zhao et al. |
| 2019/0134091 A1 | 5/2019 | Dropulic et al. |
| 2019/0151363 A1 | 5/2019 | Brentjens et al. |
| 2019/0263908 A1 | 8/2019 | Van Der Vliet et al. |
| 2020/0390876 A1 | 12/2020 | Manting et al. |
| 2020/0397883 A1 | 12/2020 | Manting et al. |
| 2021/0322471 A1 | 10/2021 | Manting et al. |
| 2021/0324332 A1 | 10/2021 | Manting et al. |
| 2021/0346479 A1 | 11/2021 | Van Wetering et al. |
| 2021/0401961 A1 | 12/2021 | Manting et al. |
| 2022/0023405 A1 | 1/2022 | Manting et al. |
| 2022/0023406 A1 | 1/2022 | Manting et al. |
| 2022/0168407 A1 | 6/2022 | Manting et al. |
| 2022/0249639 A1 | 8/2022 | Manting et al. |
| 2022/0305100 A1 | 9/2022 | Manting et al. |
| 2023/0355760 A1 | 11/2023 | Manting et al. |
| 2024/0002800 A1 | 1/2024 | Karlsson-Parra et al. |

FOREIGN PATENT DOCUMENTS

| | | |
|---|---|---|
| EP | 1894575 B1 | 2/2013 |
| EP | 2743344 A1 | 6/2014 |
| EP | 2931878 B1 | 11/2016 |
| WO | WO 1994/010202 A1 | 5/1994 |
| WO | WO 1996/007432 A1 | 3/1996 |
| WO | WO 1996/013593 A2 | 5/1996 |
| WO | WO 1996/018105 A1 | 6/1996 |
| WO | WO 1996/030046 A1 | 10/1996 |
| WO | WO 1996/040200 A1 | 12/1996 |
| WO | WO 1997/027873 A1 | 8/1997 |
| WO | WO 1998/042752 A1 | 10/1998 |
| WO | WO 1998/045332 A2 | 10/1998 |
| WO | WO 1998/054311 A1 | 12/1998 |
| WO | WO 1999/018129 A1 | 4/1999 |
| WO | WO 1999/040940 A1 | 8/1999 |
| WO | WO 2000/037504 A2 | 6/2000 |
| WO | WO 2000/054708 A1 | 9/2000 |
| WO | WO 2000/054802 A2 | 9/2000 |
| WO | WO 2001/014424 A2 | 3/2001 |
| WO | WO 2001/018636 A1 | 3/2001 |
| WO | WO 2001/049317 A2 | 7/2001 |
| WO | WO 2001/093897 A2 | 12/2001 |
| WO | WO 2002/023994 A1 | 3/2002 |
| WO | WO 2002/044395 A1 | 6/2002 |
| WO | WO 2002/044396 A1 | 6/2002 |
| WO | WO 2002/092784 A2 | 11/2002 |
| WO | WO 2003/020309 A2 | 3/2003 |
| WO | WO 2004/033685 A1 | 4/2004 |
| WO | WO 2005/012359 A2 | 2/2005 |
| WO | WO 2005/026318 A2 | 3/2005 |
| WO | WO 2005/040220 A1 | 5/2005 |
| WO | WO 2005/044853 A2 | 5/2005 |
| WO | WO 2005/044857 A1 | 5/2005 |
| WO | WO 2006/000830 A2 | 1/2006 |
| WO | WO 2006/037960 A2 | 4/2006 |
| WO | WO 2006/121168 A1 | 11/2006 |
| WO | WO 2007/011693 A2 | 1/2007 |
| WO | WO 2008/119567 A2 | 10/2008 |
| WO | WO 2009/019320 A2 | 2/2009 |
| WO | WO 2009/034172 A1 | 3/2009 |
| WO | WO 2009/046541 A1 | 4/2009 |
| WO | WO 2009/101611 A1 | 8/2009 |
| WO | WO 2009/114335 A2 | 9/2009 |
| WO | WO 2009/127988 A1 | 10/2009 |
| WO | WO 2010/037838 A2 | 4/2010 |
| WO | WO 2010/070047 A1 | 6/2010 |
| WO | WO 2011/018636 A2 | 2/2011 |
| WO | WO 2011/044186 A1 | 4/2011 |
| WO | WO 2011/143624 A2 | 11/2011 |
| WO | WO 2012/056236 A2 | 5/2012 |
| WO | WO 2012/136824 A1 | 10/2012 |
| WO | WO 2012/140130 A1 | 10/2012 |
| WO | WO 2012/145493 A2 | 10/2012 |
| WO | WO 2012/170250 A1 | 12/2012 |
| WO | WO 2013/025779 A1 | 2/2013 |
| WO | WO 2013/026833 A1 | 2/2013 |
| WO | WO 2013/026837 A1 | 2/2013 |
| WO | WO 2013/067492 A1 | 5/2013 |
| WO | WO 2013/109752 A1 | 7/2013 |
| WO | WO 2013/119714 A1 | 8/2013 |
| WO | WO 2013/126794 A1 | 8/2013 |
| WO | WO 2013/181634 A2 | 12/2013 |
| WO | WO 2014/006058 A1 | 1/2014 |
| WO | WO 2014/087010 A1 | 6/2014 |
| WO | WO 2014/087248 A2 | 6/2014 |
| WO | WO 2014/090795 A1 | 6/2014 |
| WO | WO 2014/138314 A1 | 9/2014 |
| WO | WO 2014/179664 A2 | 11/2014 |
| WO | WO 2014/186469 A2 | 11/2014 |
| WO | WO 2014/191525 A1 | 12/2014 |
| WO | WO 2014/194302 A2 | 12/2014 |
| WO | WO 2015/035606 A1 | 3/2015 |
| WO | WO 2015/073801 A1 | 5/2015 |
| WO | WO 2015/085847 A1 | 6/2015 |
| WO | WO 2015/112800 A1 | 7/2015 |
| WO | WO 2015/112900 A1 | 7/2015 |
| WO | WO 2015/191861 A1 | 12/2015 |

(56) References Cited

FOREIGN PATENT DOCUMENTS

| | | |
|---|---|---|
| WO | WO 2016/022971 A1 | 2/2016 |
| WO | WO 2016/023040 A1 | 2/2016 |
| WO | WO 2016/024021 A1 | 2/2016 |
| WO | WO 2016/081423 A1 | 5/2016 |
| WO | WO 2016/109415 A1 | 7/2016 |
| WO | WO 2016/141328 A2 | 9/2016 |
| WO | WO 2016/149201 A2 | 9/2016 |
| WO | WO 2016/154628 A1 | 9/2016 |
| WO | WO 2016/176164 A1 | 11/2016 |
| WO | WO 2016/188449 A1 | 12/2016 |
| WO | WO 2017/027422 A1 | 2/2017 |
| WO | WO 2017/049251 A2 | 3/2017 |
| WO | WO 2017/053423 A1 | 3/2017 |
| WO | WO 2017/112797 A1 | 6/2017 |
| WO | WO 2017/121771 A1 | 7/2017 |
| WO | WO 2017/134140 A1 | 8/2017 |
| WO | WO 2017/180519 A1 | 10/2017 |
| WO | WO 2017/194634 A1 | 11/2017 |
| WO | WO 2017/196793 A1 | 11/2017 |
| WO | WO 2017/215585 A1 | 12/2017 |
| WO | WO 2018/017020 A1 | 1/2018 |
| WO | WO 2018/075813 A1 | 4/2018 |
| WO | WO 2018/075857 A1 | 4/2018 |
| WO | WO 2018/075960 A1 | 4/2018 |
| WO | WO 2018/089508 A2 | 5/2018 |
| WO | WO 2018/095428 A1 | 5/2018 |
| WO | WO 2018/137705 A1 | 8/2018 |
| WO | WO 2018/233575 A1 | 12/2018 |
| WO | WO 2019/027903 A1 | 2/2019 |
| WO | WO 2019/034895 A1 | 2/2019 |
| WO | WO 2019/042119 A1 | 3/2019 |
| WO | WO 2019/042285 A1 | 3/2019 |
| WO | WO 2019/042470 A1 | 3/2019 |
| WO | WO 2019/046815 A1 | 3/2019 |
| WO | WO 2019/075385 A1 | 4/2019 |
| WO | WO 2019/086573 A1 | 5/2019 |
| WO | WO 2019/108733 A2 | 6/2019 |
| WO | WO 2019/138367 A1 | 7/2019 |
| WO | WO 2019/144895 A1 | 8/2019 |
| WO | WO 2019/157843 A1 | 8/2019 |
| WO | WO 2019/173636 A1 | 9/2019 |
| WO | WO 2019/177669 A1 | 9/2019 |
| WO | WO 2019/179366 A1 | 9/2019 |
| WO | WO 2019/184912 A1 | 10/2019 |
| WO | WO 2019/185717 A1 | 10/2019 |
| WO | WO 2019/201236 A1 | 10/2019 |
| WO | WO 2019/231846 A1 | 12/2019 |
| WO | WO 2019/238012 A1 | 12/2019 |
| WO | WO 2019/241732 A1 | 12/2019 |
| WO | WO 2020/009725 A1 | 1/2020 |
| WO | WO 2020/014366 A1 | 1/2020 |
| WO | WO 2020/017962 A1 | 1/2020 |
| WO | WO 2020/019135 A1 | 1/2020 |
| WO | WO 2020/036977 A1 | 2/2020 |
| WO | WO 2020/043188 A1 | 3/2020 |
| WO | WO 2020/208054 A1 | 10/2020 |
| WO | WO 2020/217226 A1 | 10/2020 |
| WO | WO 2021/216790 A1 | 10/2021 |

OTHER PUBLICATIONS

Vermeij et al. (Clin. Dev. Immunol. 2010: 2010: 891505; pp. 1-9).*
Ning et al. (J. Biomed. Biotechnol. 2011: 2011: 172965; pp. 1-10).*
Guo et al. (Oncol. Lett. Oct. 2012; 4 (4): 595-600).*
Gupta et al. (J. Ovarian Res. Oct. 9, 2009: 2: 13; pp. 1-20).*
Dao et al. (Oncoimmunology. 2017; 6 (2): e1252895; pp. 1-10).*
Aerts-Toegaert et al., "CD83 expression on dendritic cells and T cells: Correlation with effective immune responses", European Journal of Immunology, 37:686-695, 2007.
Agarwal et al., In Vivo Generation of CAR T Cells Selectively in Human CD4+ Lymphocytes Molecular Therapy 28(8):1783-1794 (2020).
Alemany, "Oncolytic Adenoviruses in Cancer Treatment", Biomedicines 2:36-49, 2014.
Alibakhshi et al., "Targeted cancer therapy through antibody fragments-decorated nanomedicines", J Control Release, 2017, 268: 323-334.
Alvey et al., "SIRPA-Inhibited, Marrow-Derived Macrophages Engorge, Accumulate, and Differentiate in Antibody-Targeted Regression of Solid Tumors", Current Biology, 27(14):2065-207, 2017.
Amir et al., "PRAME-Specific Allo-HLA-Restricted T Cells with Potent Antitumor Reactivity Useful for Therapeutic T-Cell Receptor Gene Transfer", Clinical Cancer Research, 17(17):5615-5625, 2011.
Andtbacka et al., "Talimogene Laherparepvec Improves Durable Response Rate in Patients With Advanced Melanoma", Journal of Clinical Oncology, 2015, 22(25): 2780-2788.
Anguille et al., "Dendritic cell vaccination as postremission treatment to prevent or delay relapse in acute myeloid leukemia", Blood, Oct. 2017, 130(15): 1713-1721.
Awate et al., "Mechanisms of action of adjuvants", Frontiers in Immunology, 4(114):1-10 (2013).
Baars et al., "Skin tests predict survival after autologous tumor cell vaccination in metastatic melanoma: Experience in 81 patients", Annals of Oncology, 11(8):965-970, 2000.
Bell et al., "Crystal structure of nucleotide-free diphtheria toxin", Biochemistry, 1997, 36(3): 481-488.
Bender et al., "Inactivated Influenza Virus, when Presented on Dendritic Cells, Elicits Human CD8+ Cytolytic T Cell Responses", J. Exp. Med. 182:1663-1671 (1995).
Bengala, et al., Mobilization; Collection, and Characterization of Peripheral Blood Hemopoietic Progenitors after Chemotherapy with Epirubicin, Paclitaxel, and Granulocyte-Colony Stimulating Factor Administered to Patients with Metastatic Breast Carcinoma; Cancer; Mar. 1, 1998; vol. 82; No. 5; pp. 867-873.
Bennett et al., "Help for cytotoxic-T-cell responses is mediated by CD40 signalling", Nature, 393:478-480 (1998).
Bergmann et al., "An endogenously synthesized decamer peptide efficiently primes cytotoxic T cells specific for the HIV-1 envelope glycoprotein", Eur J Immunol., 1993, 23(11): 2777-2781.
Bernhard et al., Generation of Immunostimulatory Dendritic Cells from Human CD34+ Hematopoietic Progenitor Cells of the Bone Marrow and Peripheral Blood, Cancer Research, 1995, pp. 1099-1104, vol. 55.
Bhaya et al., "CRISPR-Cas Systems in Bacteria and Archaea: Versatile Small RNAs for Adaptive Defense and Regulation", Annual Review Genetics, 45:273-297, 2011.
Bikard et al., "Programmable repression and activation of bacterial gene expression using an engineered CRISPR-Cas system", Nucleic Acids Research, 41(15):7429-7437, 2013.
Bommareddy et al., "Integrating oncolytic viruses in combination cancer immunotherapy", Nature Reviews Immunology, 2018, 18: 498-513.
Brocks et al., "A TNF receptor antagonistic scFv, which is not secreted in mammalian cells, is expressed as a soluble mono- and bivalent scFv derivative in insect cells", Immunotechnology 3(3):173-184 (1997).
Bürdek et al., "Three-day dendritic cells for vaccine development: Antigen uptake, processing and presentation", Journal of Translational Medicine, 8(90):1-13, 2010.
Buzzi et al., "Cancer immunity after treatment of Ehrlich tumor with diphtheria toxin", Cancer Res., Dec. 1974, 34(12): 3481-3486.
Buzzi et al., "CRM197: Effects of intravenous administration to advanced cancer patients", Cancer Res., Apr. 2004, 64(7 Supplement): 878.
Buzzi et al., "Diphtheria toxin in cancer therapy", The Lancet, 1974, 1(7858): 628-629.
Buzzi, "Diphtheria toxin treatment of human advanced cancer", Cancer Res., 1982, 42(5): 2054-2058.
Buzzi, et al., "CRM197 (nontoxic diphtheria toxin): effects on advanced cancer patients", Cancer Immunol. Immunother., 2004, 53: 1041-1048 (2004).
Buzzi, et al., "CRM197 and cancer: Effects of intratumoral administration", Therapy, Sep. 2004, 1(1): 61-66.
Buzzi, et al., "CRM197; Effects of intravenous administration to advanced cancer patients", American Association for Cancer Research, 2004, 64(7), Supplement.

(56) References Cited

OTHER PUBLICATIONS

Cermak et al, "Efficient design and assembly of custom TALEN and other TAL effector-based constructs for DNA targeting", Nucleic Acids Research, 39(12):e82-e82, 2011.
Chang et al., "A general method for facilitating heterodimeric pairing between two proteins: Application to expression of α and β T-cell receptor extracellular segments", PNAS USA 91:11408-11412 (1994).
Chao et al., "Therapeutic Targeting of the Macrophage Immune Checkpoint CD47 in Myeloid Malignancies", Frontiers in Oncology, vol. 9, Art. 1380, pp. 1-9, 2019.
Cheever et al., "The Prioritization of Cancer Antigens: A National Cancer Institute Pilot Project for the Acceleration of Translational Research", Clinical Cancer Research, 15(17):5323-5337, 2009.
Chen et al., "Enhanced proofreading governs CRISPR-Cas9 targeting accuracy", Nature, 550(7676):407-410, 2017.
Chervin et al., "Engineering higher affinity T cell receptors using a T cell display system", The Journal of Immunology Methods 339(2):175-184 (2008).
Cho et al., "Targeted genome engineering in human cells with the Cas9 RNA-guided endonuclease", Nature Biotechnology, 31(3):230-232, 2013.
Chothia et al., "The outline structure of the T-cell αβ receptor", The EMBO Journal 7(12):3745-3755 (1988).
Cignetti et al., CD34+ Acute Myeloid and Lymphoid Leukemic Blasts Can Be Induced to Differentiate Into Dendritic Cells, Blood, 1999, pp. 2048-2055, vol. 94.
Cohen et al., "Recognition of Fresh Human Tumor by Human Peripheral Blood Lymphocytes Transduced with a Bicistronic Retroviral Vector Encoding a Murine Anti-p53 TCR", The Journal of Immunology 175:5799-5808 (2005).
Cong et al., "Multiplex Genome Engineering using CRISPR/Cas Systems", Science, 339(6121):819-823, 2013.
Cougot et al., "'Cap-tabolism'", Trends in Biochemical Science 29(8):436-444, (2004).
Cripe et al., "Phase 1 Study of Intratumoral Pexa-Vec (JX-594), an Oncolytic and Immunotherapeutic Vaccinia Virus, in Pediatric Cancer Patients", Molecular Therapy, 2015, 23(3): 602-608.
Danthinne et al., Production of first generation adenovirus vectors: a review, Gene Therapy, 7(20):1707-1714, 2000.
Davila et al., "CD19 CAR-Targeted T Cells Induce Long-Term Remission and B Cell Aplasia in an Immunocompetent Mouse Model of B Cell Acute Lymphoblastic Leukemia", PLOS ONE 8(4):e61338 (2013).
Davis et al., "Basic Methods in Molecular Biology," 1986.
Davodeau et al., "Secretion of Disulfide-linked Human T-cell Receptor γδ Heterdimers", The Journal of Biological Chemistry 268(21):15455-15460 (1993).
DCPrime BV, "Leukemic Dendritic Cell Vaccination in Patients With Acute Myeloid Leukemia", ClinicalTrials.gov Identifier: NCT01373515, Retrieved from: <<https://clinicaltrials.gov/ct2/show/NCT01373515?term=NCT01373515&draw=2&rank=1>>, 5 pages, 2011.
De Gruijil et al., "Allogeneic dendritic cell (DC) vaccination as an "off the shelf" treatment to prevent or delay relapse in elderly acute myeloid leukemia patients: results of Phase I/IIa safety and feasibility study", Journal for Immunotherapy of Cancer, Supplement 1, No. P205, 2013.
Elango et al., "Optimized transfection of mRNA transcribed from a d(A/T)$_{100}$ tail-containing vector", Biochemical Biophysical Research Commun. 330:958-966 (2005).
EPO Comms, EP 08826916.2, dated Jan. 24, 2011, Jul. 20, 2012, and May 11, 2012.
Erben et al., "CS-1, A Novel c-kithi+ Acute Myeloid Leukemia Cell Line With Dendritic Cell Differentiation Capacity and Absent Immunogenicity", International Journal of Cancer, 105(2):232-240, 2003.
Ferlini et al.; A New Method to Evaluate in vitro Myelotoxicity of Antitumour Agents in the First Steps of Drug Development; Pharmacology & Toxicology 2001, 89; 231-236.

Ferrari et al.; Lack of dendritic cell mobilization into the peripheral blood of cancer patients following standard- or high-dose chemotherapy plus granulocyte-colony stimulating factor; Cancer Immunol Immunother; 2003; 52: 359-366.
Fife et al., "Inhibition of T cell activation and autoimmune diabetes using a B cell surface-linked CTLA-4 agonist", The Journal of Clinical Investigation 116(8):2252-2261 (2006).
Fiorentini et al., "Clinical experience of treatment of metastatic melanoma and solid tumours adopting a derivative of diphtheria toxin: cross-reacting material 197", In Vivo, 2013, 27(2): 197-202.
Frietze et al., "Engineering virus-like particles as vaccine platforms", Curr Opin Virol., 2016, 18: 44-49.
Gaj et al., "ZFN, TALEN, and CRISPR/Cas-based methods for genome engineering", Trends in Biotechnology, Jul. 2013, 31(7): 1-20, (Epub May 9, 2013).
Galluzzi et al., "Trial watch: Dendritic cell-based interventions for cancer therapy", OncoImmunology, 1(7):1111-1134, 2012.
Gao et al., "Selective elimination of leukemic CD34+ progenitor cells by cytotoxic T lymphocytes specific for WT1", Blood, 95(7):2198-2203, 2000.
Garboczi et al., "Assembly, Specific Binding, and Crystallization of a Human TCR-αβ with an Antigenic Tax Peptide from Human T Lymphotropic Virus Type 1 and the Class I MHC Molendule HLA-A2$^1$", The Journal of Immunology 157(12):5403-5410 (1996).
Garboczi et al., "Structure of the complex between human T-cell receptor, viral peptide and HLA-A2", Nature 384(6605):134-141 (1996).
Garfall et al., "T-cell phenotypes associated with effective CAR T-cell therapy in postinduction vs relapsed multiple myeloma", Blood Advances 3(19):2812-2815 (2019).
Geha et al., "The genetic basis of immunoglobulin-class switching", N Engl J Med., 1994, 330(14): 1008-1009.
Gilbert et al., "CRISPR-Mediated Modular RNA-Guided Regulation of Transcription in Eukaryotes", Cell, 154(2):442-451, 2013.
Gillis et al., "Contribution of human FcgRs to disease with evidence from human polymorphisms and transgenic animal studies", Frontiers in Immunology 5:254 (2014).
Giomarelli et al., "Inhibition of thrombin-induced platelet aggregation using human single-chain Fv antibodies specific for TREM-like transcript-I", Thromb Haemost 97(6):955-964 (2007).
Golden et al., "High-level production of a secreted, heterodimeric αβ murine T-cell receptor in *Escherichia coli*", Journal of Immunological Methods 206:163-169 (1997).
Graham et al., "A new technique for the assay of infectivity of human adenovirus 5 DNA", Virology, 1973, 52(2): 456-467.
Greiner et al., "High-dose RHAMM-R3 peptide vaccination for patients with acute myeloid leukemia, myelodysplastic syndrome and multiple myeloma", Haematologica, 95(7):1191-1197, 2010.
Greiner et al., "Identification and characterization of epitopes of the receptor for hyaluronic acid-mediated motility (RHAMM/CD168) recognized by CD8+ T Cells of HLA-A2-positive patients with acute myeloid leukemia", Blood, 106(3):938-945, 2005.
Grossardt et al., "Granulocyte-macrophage colony-stimulating factor-armed oncolytic measles virus is an effective therapeutic cancer vaccine", Human Gene Therapy, 2013, 24: 644-654.
Guba, et al., "Rapamycin inhibits primary and metastatic tumor growth by antiangiogenesis: involvement of vascular endothelial growth factor", Nature Medicine 8(2):128-135 (2002).
Haddad, "Genetically Engineered Vaccinia Viruses As Agents for Cancer Treatment, Imaging, and Transgene Delivery", Frontiers in Immunology, 2017, 7: 96.
He et al., "CCL3 and CCL20-recruited dendritic cells modified by melanoma antigen gene-1 induce anti-tumor immunity against gastric cancer ex vivo and in vivo", Journal of Experimental & Clinical Cancer Research, 2010, 29: 37.
Hermans et al., "The VITAL assay: a versatile fluorometric technique for assessing CTL- and NKT-mediated cytotoxicity against multiple targets in vitro and in vivo", Journal of Immunological Methods 285(1):25-40 (2004).
Hermanson et al., "Utilizing chimeric antigen receptors to direct natural killer cell activity", Frontiers in Immunology 6(195):1-6 (2015).

(56) References Cited

OTHER PUBLICATIONS

Himanen et al., "Crystal structure of an Eph receptor-ephrin complex", Nature 414(6866):933-938 (2001).
Hirooka et al., "Comprehensive immunotherapy combined with intratumoral injection of zoledronate-pulsed dendritic cells, intravenous adoptive activated T lymphocyte and gemcitabine in unresectable locally advanced pancreatic carcinoma: a phase I/II trial", Oncotarget, 2018, 9(2): 2838-2847.
Ho et al., "Inhibition of cocaine binding to the human dopamine transporter by a single chain anti-idiotypic antibody: its cloning, expression, and functional properties", Biochima et Biophysica Acta 1638(3):257-266 (2003).
Holler et al., "In vitro evolution of a T cell receptor with high affinity for peptide/MHC", PNAS USA 97(10):5387-5392 (2000).
Holler et al., "TCRs with high affinity for foreign pMHC show self-reactivity", Nature Immunology 4(1):55-62 (2003).
Howells et al., "Oncolytic Viruses—Interaction of Virus and Tumor Cells in the Battle to Eliminate Cancer", Front Oncol., 2017, 7: 195.
Hu et al., "Evolved Cas9 variants with broad PAM compatibility and high DNA specificity", Nature, 556(7699):57-63, 2018.
Huang et al., "MIR-708 promotes phagocytosis to eradicate T-ALL cells by targeting CD47", Molecular Cancer, Jan. 24, 2018, 17(12): 1-6.
Huck et al., "Sequence of a human immunoglobulin gamma 3 heavy chain constant region gene: comparison with the other human Cγ genes", Nucleic Acids Research 14(4):1779-1789 (1986).
Hudecek et al., "The Nonsignaling Extracellular Spacer Domain of Chimeric Antigen Receptors Is Decisive for In Vivo Antitumor Activity", Cancer Immunology Research 3(2):125-135 (2015).
Huston et al., "Protein engineering of antibody binding sites: Recovery of specific activity in an anti-digoxin single-chain Fv analogue produced in *Escherichia coli*", PNAS USA 85:5879-5883 (1988).
Hutzler et al., "Antigen-specific oncolytic MV-based tumor vaccines through presentation of selected tumor-associated antigens on infected cells or virus-like particles", Scientific Reports, 2017, 7: 16892.
Hwang et al., "Controlled differentiation of stem cells", Advanced Drug Delivery Reviews, 60(2):199-214, 2007.
International Search Report and Written Opinion for PCT International Application No. PCT/IB2020/053898, mailed Jul. 2, 2020.
International Search Report and Written Opinion for PCT International Application No. PCT/IB2021/052542, mailed Jun. 25, 2021.
International Search Report and Written Opinion for PCT International Application No. PCT/IB2021/055822, mailed Sep. 30, 2021.
International Search Report and Written Opinion for PCT International Application No. PCT/NL2019/050451, mailed Oct. 4, 2019.
International Search Report and Written Opinion for PCT International Patent Application No. PCT/EP2008/065391, mailed Feb. 26, 2009.
International Search Report and Written Opinion for PCT International Patent Application No. PCT/EP2013/076067, mailed Feb. 5, 2014.
International Search Report and Written Opinion for PCT International Patent Application No. PCT/IB2021/052543, mailed May 31, 2021.
International Search Report and Written Opinion for PCT International Patent Application No. PCT/IB2021/060233, mailed Apr. 4, 2022.
International Search Report and Written Opinion for PCT International Patent Application No. PCT/IB2022/050555, mailed Apr. 20, 2022.
International Search Report and Written Opinion for PCT International Patent Application No. PCT/IB2022/052211 mailed Jul. 19, 2022.
Jinek et al., "RNA-programmed genome editing in human cells", eLife, 2:e00471, 2013.
Jores et al., "Resolution of hypervariable regions in T-cell receptor β chains by a modified Wu-Kabat index of amino acid diversity", PNAS USA 87:9138-9142 (1990).
Jurincic-Winkler et al., "Antibody response to keyhole limpet hemocyanin (KLH) treatment in patients with superficial bladder carcinoma", Anticancer Res., 1996, 16(4A): 2105-2110.
Kalinski et al., "Consensual immunity: success-driven development of T-helper-1 and T-helper-2 responses", Nature Review 5:251-260 (2005).
Kleinstiver et al., "High-fidelity CRISPR-CAS9 variants with undetectable genome-wide off-targets," Nature, 529(7587):490-495, 2016.
Kloosterman et al., "Deciphering the pathogenic consequences of chromosomal aberrations in human genetic disease", Molecular Cytogenetics, 7(100):1-12, 2014.
Kochenderfer et al., "Construction and Pre-clinical Evaluation of an Anti-CD19 Chimeric Antigen Receptor", Journal of Immunotherapy 32(7):689-702 (2009).
Kohrt et al., "Donor immunization with WT1 peptide augments antileukemic activity after MHC-matched bone marrow transplantation", Blood, 118(19):5319-5329, 2011.
Kotb, "Bacterial Pyrogenic Exotoxins as Superantigens", Clinical Microbiology Reviews 8(3):411-426 (1995).
Koup et al., "Vaccine design for CD8 T lymphocyte responses", Cold Spring Harb Perspect Med., 2011, 1(1): a007252.
Krug et al., "WT1 Peptide Vaccinations Induce CD4 and CD8 T Cell Immune Responses in Patients With Mesothelioma and Non-small Cell Lung Cancer", Cancer Immunology, Immunotherapy, 59(10):1467-1479, 2010.
Kruisbeek, "Adoption of Cryostor® in Manufacturing of a Dendritic Cell Vaccine Platform", BioPreservation Today®, vol. 3, Issue 1, p. 10, 2011.
Kudo-Saito, et al., "Intratumoral vaccination and diversified subcutaneous/intratumoral vaccination with recombinant poxviruses encoding a tumor antigen and multiple costimulatory molecules", Clin Cancer Res., 2004, 10(3): 1090-1099.
Kurtzberg et al., "CD7+, CD4−, CD8-Acute Leukemia: A Syndrome of Malignant Pluripotent Lymphohematopoietic Cells", Blood, 73(2):381-390, 1989.
Lal et al., "Recombinant viruses with other anti-cancer therapeutics: a step towards advancement of oncolytic virotherapy", Cancer Gene Ther., 2018, 25: 216-226.
Larsson et al., "Functional and transcriptional profiling of MUTZ-3, a myeloid cell line acting as a model for dendritic cells", Immunology, 117:156-166, 2006.
Laurell et al., "Intratumorally injection pro-inflammatory allogeneic dendritic cells as immune enhancers: a first in-human study in unfavourable risk patients with metastatic renal cell carcinoma", Journal for Immunotherapy of Cancer 5:52 (2017).
Lawler et al., "Oncolytic Viruses in Cancer Treatment: A Review", JAMA Oncol. Review, 2017, 3(6): 841-849.
Leaf et al., "DCOne as an Allogeneic Cell-based Vaccine for Multiple Myeloma", Journal of Immunotherapy 40(9):315-322 (2017).
Lee et al., "ASTCT Consensus Grading for Cytokine Release Syndrome and Neurologic Toxicity Associated with Immune Effector Cells", Biology of Blood and Marrow Transplantation 25:625-638, doi.org/10.1016/j.bbmt.2018.12.758 (2019).
Lefranc et al., "IMGT unique numbering for immunoglobulin and T cell receptor variable domains and Ig superfamily V-like domains", Developmental and Comparative Immunology 27:55-77 (2003).
Li et al., "Directed evolution of human T-cell receptors with picomolar affinities by phage display", Nature Biotechnology 23(3):349-354 (2005).
Li et al., "Vaccination with CD47 deficient tumor cells elicits an antitumor immune response in mice", Nature Communications, 11:581, 2020.
Liu et al., "Pre-Clinical Development of a Humanized Anti-CD47 Antibody with Anti-Cancer Therapeutic Potential", PLoS One, 10(9): e0137345, 2015.
Logtenberg et al., "Glutaminyl cyclase in an enzymatic modifier of the CD47-SIRPα axis and target for cancer immunotherapy", Nat. Med., 25(4):612-619, 2019.
Lu et al., "Potential New Cancer Immunotherapy: Anti-CD47-SIRPα Antibodies", OncoTargets and Therapy, 13:9323-9331, 2020.
Lundstrom, K., "Viral Vectors in Gene Therapy", Diseases 6(2):42, DOI: 10.3390/diseases6020042 (2018).

(56) References Cited

OTHER PUBLICATIONS

Ma et al., "Preclinical development of a novel CD47 nanobody with less toxicity and enhanced anti-cancer therapeutic potential", Journal of Nanobiotechnology, 18:12, pp. 1-15, 2020.
Mali et al., "CAS9 transcriptional activators for target specificity screening and paired nickases for cooperative genome engineering", Nature Biotechnology, 31(9):833-838, 2013.
Mali et al., "RNA-Guided Human Genome Engineering via Cas9", Science, 339(6121):823-826, 2013.
Malito et al., "Structural basis for lack of toxicity of the diphtheria toxin mutant CRM197", Proc Natl Acad Sci U S A, 2012, 109(14): 5229-5234.
Marelli et al., "Oncolytic Viral Therapy and the Immune System: A Double-Edged Sword Against Cancer", Frontiers in Immunology, 2018, 9: 866.
Masterson et al., "MUTZ-3, a human cell line model for the cytokine-induced differentiation of dendritic cells from CD34+ precursors", Blood, 100(2):701-703, 2002.
May et al., "Peptide Epitopes From the Wilms' Tumor 1 Oncoprotein Stimulate CD4+ and CD8+ T Cells That Recognize and Kill Human Malignant Mesothelioma Tumor Cells", Clinical Cancer Research, 13(15):4547-4555, 2007.
Mishra et al., "Structural and immunological characterization of E. coli derived recombinant CRM197 protein used as carrier in conjugate vaccines", Bioscience reports, 2018, 38(5): BSR20180238.
Mitchell et al. "Tetanus toxoid and CCL3 improve dendritic cell vaccines in mice and glioblastoma patients", Nature 519(7543):366-369 (2015).
Miyamoto et al., "Heparin-binding epidermal growth factor-like growth factor as a novel targeting molecule for cancer therapy", Cancer Science 97(5):341-347 (2006).
Miyamoto, et al., "New approach to cancer therapy: heparin binding-epidermal growth factor-like growth factor as a novel targeting molecule", Anticancer Res., 2007, 27(6A): 3713-3721.
Mohan et al., "Applications of chemokines as adjuvants for vaccine immunotherapy", Immunobiology, 2018, 223(6-7): 477-485.
Moldenhauer et al., "Tumor Necrosis Factor Alpha-Stimulated Endothelium: An Inducer of Dendritic Cell Development from Hematopoietic Progenitors and Myeloid Leukemic Cells", Stem Cells, 22(2):144-157, 2004.
Montfoort et al., "NKG2A Blockade Potentiates CD8 T Cell Immunity Induced by Cancer Vaccines", Cell 175(7):1744-1755 (2018).
Moosmayer et al., "A single-chain TNF receptor antagonist is an effective inhibitor of TNF mediated cytotoxicity", Therapeutic Immunology, 2(10):31-40 (1995).
Morris, "Cryopreservation of Animal and Human Cell Lines", Methods in Molecular Biology, vol. 368: Cryopreservation and Freeze-Drying Protocols, 2nd Ed. (J. G. Day and G. N. Stacey eds.), Humana Press Inc. Totowa, N.J., pp. 227-236, .2007.
Moya et al., "Inhibition of Coated Pit Formation in Hep2 Cells Blocks the Cytotoxicity of Diphtheria Toxin But Not That of Ricin Toxin", The Journal of Cell Biology 101(2):548-559 (1985).
Mumtaz et al., "Design of liposomes for circumventing the reticuloendothelial cells", Glycobiology 1(5):505-510 (1991).
Murata et al., "CD47-signal regulatory protein α signaling system and its application to cancer immunotherapy", Cancer Sci., Aug. 2018, 109(8): 2349-2357 (Epub Jul. 4, 2018).
Nacheva et al., "Preventing nondesired RNA-primed RNA extension catalyzed by T7 RNA polymerase", Eur. J. Biochem. 270:1485-1465 (2003).
Nagasawa et al., "DCP-001 stimulates T cell proliferation and increases memory CD4 + T cells in OC patients' PBMC Preclinical studies support therapeutic application of the leukemic cell-based cancer relapse vaccine DCP-001 in ovarian cancer", Nov. 1, 2020, Retrieved from the Internet: URL:https://immunicum.se/wp-content/uploads/2021/04/Poster-DCprime_SITC2020-FINAL.pdf.
Nagasawa et al., "Preclinical studies support therapeutic application of the leukemic cell-based cancer relapse vaccine DCP-001 in ovarian cancer", Journal for Immunotherapy Cancer 8(Suppl. 3): A102-A103 (Abstract 171) (2020).
Nam, et al., "Anti-tumor Effect of Intravenous Administration of CRM197 for Triple-negative Breast Cancer Therapy", Anticancer Res., 2016, 36(7): 3651-3657.
Narita et al., "WT1 Peptide Vaccination in Combination With Imatinib Therapy for a Patient With CML in the Chronic Phase", International Journal of Medical Sciences, 7(2):72-81, 2010.
Neelapu et al., "Chimeric antigen receptor T-cell therapy—assessment and management of toxicities", Nat Rev Clin Oncology 15(1):47-62 (2018).
Neuhaus et al., Multiple sclerosis: Mitoxantrone promotes differential effects on immunocompetent cells in vitro; Journal of Neuroimmunology 168: 128-137 (2005).
Nguyen-Hoai et al., "CCL21 (SLC) improves tumor protection by a DNA vaccine in a Her2/neu mouse tumor model", Cancer Gene Therapy, 2012, 19: 69-76.
Nijman et al., "Phase 1 Study to Evaluate the Safety, Feasibility and Immunogenicity of an Allogeneic, Cell-based Vaccine (DCP-001) in High Grade Serous Ovarian Cancer Patients After Primary Treatment (ALISON)", Feb. 4, 2021, Retrieved from the Internet: URL:https://clinicaltrials.gov/ct2/show/NCT04739527.
Ochsenreither et al., "Wilms Tumor Protein 1 (WT1) Peptide Vaccination-induced Complete Remission in a Patient With Acute Myeloid Leukemia is Accompanied by the Emergence of a Predominant T-cell Clone Both in Blood and Bone Marrow", Journal of Immunotherapy, 34(1):85-91, 2011.
Olusanya et al., "Liposomal Drug Delivery Systems and Anticancer Drugs", Molecules, 2018, 23(4): 907.
Palucka et al., "Recent Developments in Cancer Vaccines", The Journal of Immunology, 186(3):1325-1331, 2011.
Park et al., "Are All Chimeric Antigen Receptors Created Equal?", Journal of Clinical Oncology 33(6):651-653 (2015).
Parkhurst et al., "Characterization of Genetically Modified T-Cell Receptors that Recognize the CEA:691-699 Peptide in the Context of HLA-A2.1 on Human Colorectal Cancer Cells", Clinical Cancer Research 15(1):169-180 (2009).
Pashine et al., "Targeting the innate immune response with improved vaccine adjuvants", Nature Medicine Supplement 11(4): S63-S68 (2005).
Peter et al., "Protective effects of an anti-melanocortin-4 receptor scFv derivative in lipopolysaccharide-induced cachexia in rats", J Cachexia Sarcopenia Muscle Aug. 12, 2012.
Peter et al., "scFv Single Chain Antibody Variable Fragment as Inverse Agonist of the $β_2$-Adrenergic Receptor", The Journal of Biological Chemistry 278(38):36740-36747 (2003).
Popkov et al., "Human/mouse cross-reactive anti-VEGF receptor 2 recombinant antibodies selected from an immune b9 allotype rabbit antibody library", Journal of Immunological Methods 288:149-164 (2004).
Presta et al., "Humanization of an Anti-Vascular Endothelial Growth Factor Monoclonal Antibody for the Therapy of Solid Tumors and Other Disorders", Cancer Research 57:4593-4599 (1997).
Qi et al., "Repurposing CRISPR as an RNA-Guided Platform for Sequence-Specific Control of Gene Expression", Cell, 152(5):1173-1183, 2013.
Quintarelli et al., "Cytotoxic T lymphocytes directed to the preferentially expressed antigen of melanoma (PRAME) target chronic myeloid leukemia", Blood, 112(5):1876-1885, 2008.
Quintarelli et al., "High-avidity cytotoxic T lymphocytes specific for a new PRAME-derived peptide can target leukemic and leukemic-precursor cells", Blood, 117(12):3353-3362, 2011.
Rezvani et al., "Leukemia-associated antigen-specific T-cell responses following combined PR1 and WT1 peptide vaccination in patients with myeloid malignancies", Blood, 111(1):236-242, 2008.
Rezvani et al., "T-Cell Responses Directed against Multiple HLA-A* 0201-Restricted Epitopes Derived from Wilms' Tumor 1 Protein in Patients with Leukemia and Healthy Donors: Identification, Quantification, and Characterization", Clinical Cancer Research, 11(24):8799-8807, 2005.
Rosato et al., "Virus-specific memory T cells populate tumors and can be repurposed for tumor immunotherapy", Nature Communications 10:567 (2019).

(56) References Cited

OTHER PUBLICATIONS

Rosenberg "Cell transfer immunotherapy for metastatic solid cancer—what clinicians need to know", Nat Rev Clinical Oncology 8(10):577-585 (2011).
Rosenfeld et al., "WT1 in acute leukemia, chronic myelogenous leukemia and myelodysplastic syndrome: therapeutic potential of WT1 targeted therapies", Leukemia, 17:1301-1312, 2003.
Santegoets et al., "A CD34+ Human cell line model of myeloid dendritic cell differentiation: evidence for a CD14+CD11b+ Langerhans cell precursor", Journal of Leukocyte Biology, 80:1337-1344, 2006.
Santegoets et al., "In vitro priming of tumor-specific cytotoxic T lymphocytes using allogeneic dendritic cells derived from the human MUTZ-3 cell line", Cancer Immunology, Immunotherapy, 55:1480-1490, 2006.
Saxena et al., "Re-emergence of Dendritic Cell Vaccines for Cancer Treatment", Trends in Cancer, 2018, 4:2: 119-137.
Schenborn et al., "A novel transcription property of SP6 and T7 RNA polymerases: dependence on template structure", Nucleic Acids Research 13:6223-36 (1985).
Scheraga "Predicting Three-Dimensional Structures of Oligopeptides" Reviews in Computational Chemistry 2:73-142 (1992).
Schlueter et al., "Specificity and Binding Properties of a Single-chain T Cell Receptor", J. Mol. Biol. 256:859-869 (1996).
Schmitt et al., "Chronic myeloid leukemia cells express tumor-associated antigens eliciting specific CD8+ T-cell responses and are lacking costimulatory molecules", Experimental Hematology, 34(12):1709-1719, 2006.
Schmitt et al., "RHAMM-R3 peptide vaccination in patients with acute myeloid leukemia, myelodysplastic syndrome, and multiple myeloma elicits immunologic and clinical responses", The Journal of the American Society of Hematology, 111(3):1357-1365, 2008.
Shankar et al., "Interferon-[gamma] Added During Bacillus Calmette-Guerin Induced Dendritic Cell Maturation Stimulates Potent T h 1 Immune Responses", Oct. 10, 2003, Retrieved from the Internet: URL:https://link.springer.com/content/pdf/10.1186/1479-5876-1-7.pdf.
Shen et al. "Engineering Peptide Linkers for scFv Immunosensors", Anal. Chem. 80(6):1910-1917 (2008).
Shieh et al., "Transgenic Expression of Single-Chain Anti-CTLA-4 Fv on β Cells Protects Nonobese Diabetic Mice from Autoimmune Diabetes", The Journal of Immunology 183(4):2277-2285 (2009).
Slaymaker et al., "Rationally engineered Cas9 nucleases with improved specificity", Science, 351(6268):84-88, 2016.
Smith, et al., "In situ programming of leukaemia-specific T cells using synthetic DNA nanocarriers", Nat. Nanotechnology 12(8):813-820 (2017).
Sockolosky et al., "Durable antitumor responses to CD47 blockade require asaptive immune stimulation", PNAS, 113(19):E2646-2654, 2016.
Sommandas et al., "Novel vaccination strategies using tumour-independent antigens to induce anti-tumour immunity in solid tumours", https://dcprime.com/wp-content/uploads/2018/07/Poster-FINAL-DCprime_SITC2019-NOV2019.pdf [retrieved on Apr. 4, 2022] poster.
Sommandas et al., "Novel vaccination strategies using tumour-independent antigens to induce anti-tumour immunity in solid tumours", Journal for Immunotherapy of Cancer 7(Suppl. 1):p. 687 (2019) & 34th Annual Meeting of the Society for Immunotherapy of Cancer, National Harbour, MD, USA, Nov. 10, 2019.
Sommermeyer et al., "Chimeric antigen receptor-modified T cells derived from defined CD8+ and CD4+ subsets confer superior antitumor reactivity in vivo", Leukemia 30(2):492-500 (2016).
Stepinski et al., "Synthesis and properties of mRNAs containing the novel "anti-reverse" cap analogs 7-methyl(3'-O-methyl)GpppG and 7-methyl(3'-deoxy)GpppG", RNA, 7:1468-1495 (2001).
Stickings, et al., "Transcutaneous immunization with cross-reacting material CRM(197) of diphtheria toxin boosts functional antibody levels in mice primed parenterally with adsorbed diphtheria toxoid vaccine", Infect Immun., 2008, 76(4):1766-1773.
Subhadra et al., "Inducing Tumor Suppressive Microenvironments through Genome Edited CD47-/- Syngeneic Cell Vaccination", Scientific Reports, Dec. 27, 2019, 9(1): 20057.
Suhrbier, "Multi-epitope DNA vaccines", Immunol Cell Biol., 1997, 75(4): 402-408.
Tack et al., "Phenotypic and genomic analysis of an exceptional case of enteropathy associated T-cell lymphoma", Leukemia Research, 34(8):e183-e189, 2010.
Tacken et al., "Effective induction of naive and recall T-cell responses by targeting antigen to human dendritic cells via a humanized anti-DC-SIGN antibody", Blood, 2005, 106(4): 1278-1285.
Tan et al., "Influence of the hinge region on complement activation, C1q binding, and segmental flexibility in chimeric human immunoglobulins", PNAS USA 87(1):162-166 (1990).
Teachey et al. "Identification of Predictive Biomarkers for Cytokine Release Syndrome afer Chimeric Antigen Receptor T-cell Therapy for Acute Lymphoblastic Leukemia", Cancer Discovery 6(6):664-679 (2016).
Temizoz et al., "Vaccine adjuvants as potential cancer immunotherapeutics", International Immunology 28(7):329-338 (2016).
Themeli et al., "Generation of tumor-targeted human T lymphocytes from induced pluripotent stem cells for cancer therapy", Nature Biotechnology 31(10):928-933 (2013).
Thurner et al., "Generation of large numbers of fully mature and stable dendritic cells from leukapheresis products for clinical application", Journal of Immunological Methods, 223(1):1-15, 1999.
Topfer et al., "DAP12-Based Activating Chimeric Antigen Receptor for NK Cell Tumor Immunotherapy", The Journal of Immunology 194(7):3201-3212 (2015).
Triozzi et al., "Intratumoral injection of dendritic cells derived in vitro in patients with metastatic cancer", Cancer, 2000, 89(12): 2646-2654.
Tseng et al., "Anti-CD47 antibody-mediated phagocytosis of cancer by macrophages primes an effective antitumor T-call response", PNAS, 110(27):11103-11108, 2013.
Tsukahara et al., "CD19 target-engineered T-cells accumulate at tumor lesions in human B-cell lymphoma xenograft mouse models", Biochem Biophys Res Commun 438(1):84-89 (2013).
Twumasi-Boateng et al., "Oncolytic viruses as engineering platforms for combination immunotherapy", Nature Reviews Cancer 18:419-432 (2018).
Uchida et al., "Mutation in the structural gene for diphtheria toxin carried by temperate phage", Nat New Biol., 1971, 233(35): 8-11.
Ud Din et al., "Effective use of nanocarriers as drug delivery systems for the treatment of selected tumors", Int J Nanomedicine, 2017, 12: 7291-7309.
Ueno et al., "Harnessing Human Dendritic Cell Subsets for Medicine", Immunological Reviews, 234(1):199-212, 2010.
Van De Loosdrecht et al., "A novel allogeneic off-the-shelf dendritic cell vaccine for post-remission treatment of elderly patients with acute myeloid leukemia", Cancer Immunology, Immunotherapy 67(10):1505-1518 (2018).
Van De Ven et al., "Exposure of CD34+ precursors to cytostatic anthraquinone-derivatives induces rapid dendritic cell differentiation: implications for cancer immunotherapy", Cancer Immunology, Immunotherapy, Springer, Berlin, DE, 61(2):181-191, 2011.
Van Helden et al., "Human and murine model cell lines for dendritic cell biology evaluated", Immunology Letters, 117(2):191-197, 2008.
Van Nuffel et al., "Loading of dendritic cells for immunotherapy", ISBT Science Series, 2013, 8: 161-164.
Van Tendeloo et al., "Induction of complete and molecular remissions in acute myeloid leukemia by Wilms' tumor 1 antigen-targeted dendritic cell vaccination", PNAS, 107(31):13824-13829, 2010.
Varela-Rohena et al., "Control of HIV-1 immune escape by CD8 T-calls expressing enhanced T-cell receptor", Nat Med. 14(12):1390-1395 (2008).
Vermeij et al., "Potential Target Antigens for a Universal Vaccine in Epithelial Ovarian Cancer", Clinical and Developmental Immunology, vol. 2010, Article ID 891505, pp. 1-8. 2010.
Vigneron et al., "Database of T cell-defined human tumor antigens: the 2013 update", Cancer Immunity, 2013, 13: 15.

(56) References Cited

OTHER PUBLICATIONS

Wadelin et al., "Leucine-rich repeat protein PRAME: expression, potential functions and clinical implications for leukemia", Molecular Cancer, 9(1):1-10, 2010.
Wallgren et al., "Direct Allorecognition Promotes Activation of Bystander Dendritic Cells and Licenses Them for Th1 Priming: A Functional Link Between Direct and Indirect Allosensitization", Scandinavian Journal of Immunology 62:234-242 (2005).
Wang et al., "CMVpp65 Vaccine Enhances the Antitumor Efficacy of Adoptively Transferred CD19-Redirected CMV-Specific T Cells", Clinical Cancer Research 21(13):2993-3002 (2015).
Weiskopf et al., "CD47-blocking immunotherapies stimulate macrophage-mediated destruction of small-cell lung cancer", Journal of Clinical Investigation, 126(7):2610-2620, 2016.
Weiskopf et al., "Engineered SIRPα Variants as Immunotherapeutic Adjuvants to Anticancer Antibodies", Science, 341(6141):88-91, 2013.
Welte et al., "Purification and biochemical characterization of human pluripotent hematopoietic colony-stimulating factor", PNAS, 82(5): 1526-1530, 1985.
Westers et al., Rapid generation of antigen-presenting cells from leukaemic blasts in acute myeloid leukaemia, Cancer Immunology, Immunotherapy. 2003, pp. 17-27, vol. 52.
Wlodarska et al., "A New Subtype of Pre-B Acute Lymphoblastic Leukemia With t(5;12)(q31q33;p12), Molecularly and Cytogenetically Distinct From t(5;12) in Chronic Myelomonocytic Leukemia", Blood, 89(5):1716-1722, 1997.
Xie et al., "Direct demonstration of MuSK involvement in acetylcholine receptor clustering through identification of agonist ScFv", Nature Biotechnology 15(8):768-771 (1997).
Yan et al., "Engineering Upper Hinge Improves Stability and Effector Function of a Human IgG1", The Journal of Biological Chemistry 287(8):5891-5897 (2012).
Yilmaz et al., Activated myeloid dendritic cells accumulate and colocalize with CD3+ T cells in coronary artery lesions in patients with Kawasaki disease, Experimental Molecular Pathology 2007, pp. 93-103, vol. 83, No. 1.
Zhang et al., "Advances in Anti-Tumor Treatments Targeting the CD47/SIRPα Axis", Frontiers Immunology, vol. 11, Art. 18, pp. 1-15, 2020.
Zhang et al., "An NKp30-Based Chimeric Antigen Re3ceptor Promotes T Cell Effector Functions and Antitumor Efficacy In Vivo", The Journal of Immunology 189(5):2290-2299 (2012).
Zhao et al., "Characteristics of an scFv Antibody Fragment That Binds to Immunoglobulin G of Graves' Disease Patients and Inhibits Autoantibody-Mediated Thyroid-Stimulating Activity", Hybridoma 27(6):455-451 (2008).
Zhao et al., "Multiple injections of electroporated autologous T cells expressing a chimeric antigen receptor mediate regression of human disseminated tumor", Cancer Research 70(22):9053-9061 (2010).
Zhou et al., "Exclusive Transduction of Human CD4+ T Cells upon Systemic Delivery of CD4-Targeted Lentiviral Vectors", The Journal of Immunology 195(5):2493-2501 (2015).
Zhou et al., "T-cell receptor gene transfer exclusively to human CD8+ cells enhances tumor cell killing", Blood 120(22):4334-4342 (2012).
Zibera, et al.; An epirubicin/paclitaxel combination mobilizes large amounts of hematopoietic progenitor cells in patients with metastatic breast cancer showing optimal response to the same chemotherapy regimen; Haematologica 1999; 84:924-929.
Zuo et al., "Transfer of Cellular Content from the Allogeneic Cell-Based Cancer Vaccine DCP-001 to Host Dendritic Cells Hinges on Phosphatidylserine and Is Enhanced by CD47 Blockade", Cells, Nov. 19, 2021, 10(11): 3233.
Akahori et al., "Antitumor of CAR-T cells targeting the intracellular onco-protein WT1 can be enhanced by vaccination", Blood, 2018, 132(11): 1134-1145.
Dranoff et al., "Vaccination with irradiated tumor cells engineered to secrete murine granulocyte-macrophage colony-stimulating factor stimulates potent, specific, and long-lasting anti-tumor immunity", PNAS USA, Apr. 1993, 90: 3539-3543.
Trivedi et al., "Generation of CMV-specific T lymphocytes using protein-spanning pools of pp65-derived overlapping pentadecapeptides for adoptive immunotherapy", Blood, 2005, 105(7): 2793-2801.
Batich et al., "Long-term Survival in Glioblastoma with Cytomegalovirus pp65-Targeted Vaccination", Clin Cancer Res., Apr. 15, 2017, 23(8): 1898-1909.
Granzin et al., "Shaping of Natural Killer Cell Antitumor Activity by Ex Vivo Cultivation", Frontiers in Immunology, Apr. 26, 2017, 8: 18 pages.
International Search Report and Written Opinion for PCT International Patent Application No. PCT/IB2023/052272 mailed Jun. 21, 2023.
International Search Report and Written Opinion for PCT International Patent Application No. PCT/IB2023/054997, mailed Aug. 11, 2023.
International Search Report and Written Opinion for PCT International Patent Application No. PCT/IB2023/061000 mailed Jan. 24, 2023.
Ji et al., "Aberrant expression of CD133 and CD82 in patients with pediatric acute lymphoblastic leukemia and the clinical significance", Oncol Lett, Nov. 2017, 14(5): 5811-5818.
Laurenti et al., "From haematopoietic stem cells to complex differentiation landscapes", Nature, 2018, 553(7689): 418-426.
Nobuoka et al., "Intratumoral peptide injection enhances tumor cell antigenicity recognized by cytotoxic T lymphocytes: a potential option for improvement in antigen-specific cancer immunotherapy", Cancer Immunol Immunother., Apr. 2013, 62(4): 639-652.
Sikic et al., "First-in-Human, First-in-Class Phase I Trial of the Anti-CD47 Antibody Hu5F9-G4 in Patients With Advanced Cancers", J Clin Oncol., Apr. 20, 2019, 37(12): 946-953.
Skopek et al., "Choosing the Right Cell Line for Acute Myeloid Leukemia (AML) Research", Int J Mol Sci., 2023, 24(5377): 1-34.
Tanaka et al., "Recent progress in and challenges in cellular therapy using NK cells for hematological malignancies", Blood Reviews, Mar. 20, 2020, 44: 100678.
Van De Loosdrecht et al., "Clinical Study Protocol an International Multicentre, Open-Label Study to Evaluate the Efficacy and Safety of Two Different Vaccination Regimens of Immunotherapy with Allogeneic Dendritic Cells, DCP-001, In Patients with Acute Myeloid Leukaemia", Aug. 27, 2018, CT Identifier: NCT03697707.
Van De Loosdrecht et al., "Use of an Allogeneic Leukemia-Derived Dendritic Cell Vaccine in MRD+ AML-Patients Results in MRD Conversion, Improved Relapse-Free Survival and Vaccine Induced Immune Responses to Tumor Antigens", Blood, Nov. 15, 2022, 140(Suppl. 1): 1714-1715.
Van De Loosdrecht et al., "Conversion from MRD Positive to Negative Status in AML Patients in CR1 after Treatment with an Allogenic Leukemia-Derived Dendritic Cell Vaccine", Blood, Nov. 5, 2020, 136(1): 13-14.
Yan et al., "Combining Immune Checkpoint Inhibitors with Conventional Cancer Therapy", Frontiers in Immunology, Jul. 2018, vol. 9, Article 1739.
Zhou et al., "LPS-treated bone marrow-derived dendritic cells induce immune tolerance through modulating differentiation of CD4+ regulatory T cell subpopulations mediated by 3G11 and CD127", Immunologic Research, 2017, 65(3): 630-638.
Zuo et al., "386-Efficient ex-vivo expansion of adaptive NKG2C+/CD57+ NK cells from CMV-positive donors using dendritic cells derived from the acute myeloid cell line DCOne", Journal for ImmunoTherapy of Cancer, Nov. 2022, 10(Suppl. 2): A407.
Sarova et al., "Characterization of Chromosome 11 Breakpoints and the Areas of Deletion and Amplification in Patients with Newly Diagnosed Acute Myeloid Leukemia", Genes, Chromosomes, & Cancer, 2013, 52: 619-635.
Marabelle et al., "Intratumoral immunotherapy: using the tumor as the remedy", Annals of Oncology, 2017, 28(Suppl. 12): xii33-xii43.
Cellosaurus entry to MVX-1, First published 2022, Retrieved from url: <https://www.cellosaurus.org/CVCL_C3M8>.
U.S. Appl. No. 12/736,920 2011/0117051 U.S. Pat. No. 8,470,789, filed Nov. 19, 2010 May 19, 2011 Jun. 25, 2013, Sandra Van Wetering, Method for Inducing and Accelerating Cells.

(56) References Cited

OTHER PUBLICATIONS

U.S. Appl. No. 14/648,210 2015/0297698 U.S. Pat. No. 10,064,923, filed May 28, 2015 Oct. 22, 2015 Sep. 4, 2018, Sandra Van Wetering, Therapeutic Cancer Vaccines Derived from a Novel Dendritic Cell Line.
U.S. Appl. No. 16/101,028 2019/0000945 U.S. Pat. No. 11,027,001, filed Aug. 10, 2018 Jan. 3, 2019 Jun. 8, 2021, Sandra Van Wetering, Therapeutic Cancer Vaccines Derived from a Novel Dendritic Cell Line.
U.S. Appl. No. 17/239,097 2021/0346479, filed Apr. 23, 2021 Nov. 11, 2021, Sandra Van Wetering, Therapeutic Cancer Vaccines Derived from a Novel Dendritic Cell Line.
U.S. Appl. No. 16/857,851 2020/0390876 U.S. Pat. No. 11,052,144, filed Apr. 24, 2020 Dec. 17, 2020 Jul. 6, 2021, Erik Hans Manting, Methods of Tumor Vaccination.
U.S. Appl. No. 17/342,893 2021/0401961, filed Jun. 9, 2021 Dec. 30, 2021, Erik Hans Manting, Methods of Tumor Vaccination.
U.S. Appl. No. 16/858,326 2020/0397883 U.S. Pat. No. 11,071,778, filed Apr. 24, 2020 Dec. 24, 2020 Jul. 27, 2021, Erik Hans Manting, Combination Product for Use in Tumor Vaccination.
U.S. Appl. No. 17/361,462 2022/0023406, filed Jun. 29, 2021 Jan. 27, 2022, Erik Hans Manting, Combination Product for Use in Tumor Vaccination.
U.S. Appl. No. 18/119,487 2023/0355760, filed Mar. 9, 2023 Nov. 9, 2023, Erik Hans Manting, Modified Cells of Leukemic Origin and a PD-L1 Antibody for Enhancing the Efficacy of Cancer Cell Therapy.
U.S. Appl. No. 17/361,477 2022/0023405, filed Jun. 29, 2021 Jan. 27, 2022, Erik Hans Manting, Use Of Leukemia-Derived Cells In Ovarian Cancer Vaccines.
U.S. Appl. No. 17/213,460 2021/0322471, filed Mar. 26, 2021 Oct. 21, 2021, Erik Hans Manting, In Vivo Use Of Modified Cells Of Leukemic Origin For Enhancing The Efficacy Of Adoptive Cell Therapy.
U.S. Appl. No. 17/213,461 2021/0324332 U.S. Pat. No. 12,091,681, filed Mar. 26, 2021 Oct. 21, 2021 Sep. 17, 2024, Erik Hans Manting, Ex Vivo Use Of Modified Cells Of Leukemic Origin For Enhancing The Efficacy Of Adoptive Cell Therapy.
U.S. Appl. No. 18/804,310, filed Aug. 14, 2024, Erik Hans Manting, Ex Vivo Use Of Modified Cells Of Leukemic Origin For Enhancing The Efficacy Of Adoptive Cell Therapy
U.S. Appl. No. 17/519,101 2022/0168407, filed Nov. 4, 2021 Jun. 2, 2022, Erik Hans Manting, Use Of Tumor-Independent Antigens In Immunotherapies.
U.S. Appl. No. 17/580,919 2022/0249639, filed Jan. 21, 2022 Aug. 11, 2022, Erik Hans Manting, Methods of Tumor Vaccination.
U.S. Appl. No. 17/692,321 2022/0305100, filed Mar. 11, 2022 Sep. 29, 2022, Erik Hans Manting, Methods Of Vaccination And Use Of CD47 Blockade.
U.S. Appl. No. 18/499,357 2024/0173408, filed Nov. 1, 2023 May 30, 2024, Jeroen Rovers, Prognostic Biomarkers For Cancer Relapse Vaccination And Methods Of Use Thereof.
U.S. Appl. No. 18/197,670 2024/0002800, filed May 15, 2023 Jan. 4, 2024, Alex Karlsson-Parra, Use of Leukemia-Derived Cells for Enhancing Natural Killer (NK) Cell Therapy.
Fellermann et al., "Super-resolution microscopy unveils transmembrane domain- mediated internalization of cross-reacting material 197 into diphtheria toxin-resistant mouse J774A.1 cells and primary rat fibroblasts in vitro", Arch Toxicol., May 2020, 94(5): 1753-1761.
Schmid, "A nostalgic look back 40 years after the discovery of receptor-mediated endocytosis", Mol Biol Cell., Jan. 1, 2019, 30(1): 1-3.
Wang et al., "Diphtheria toxin mutant CRM197-mediated transcytosis across blood- brain barrier in vitro", Cell Mol Neurobiol., Jul. 2010, 30(5): 717-725, Epublished Jan. 16, 2010.
Zhang et al., "The Multiple Functions of HB-EGF in Female Reproduction and Related Cancer: Molecular Mechanisms and Targeting Strategies", Reprod Sci., Sep. 2024, 31(9): 2588-2603, Epublished Feb. 29, 2024.

\* cited by examiner

FIG. 4
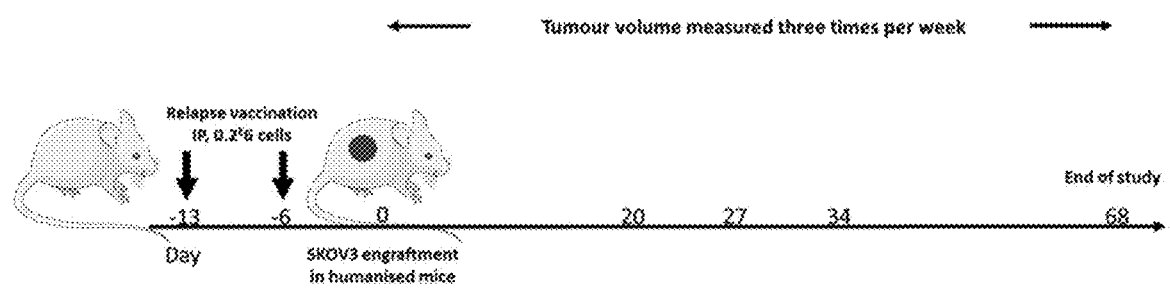
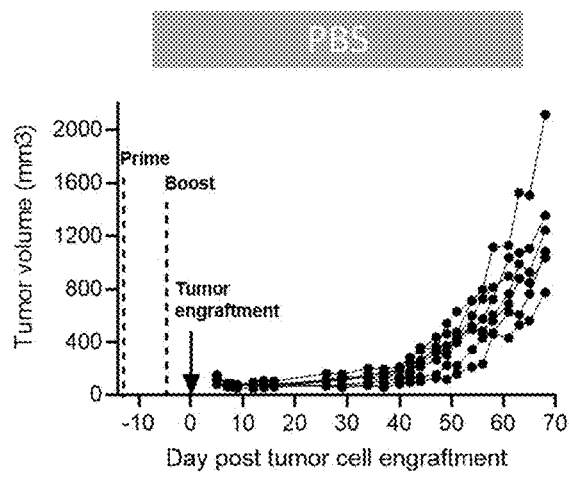
FIG. 5A
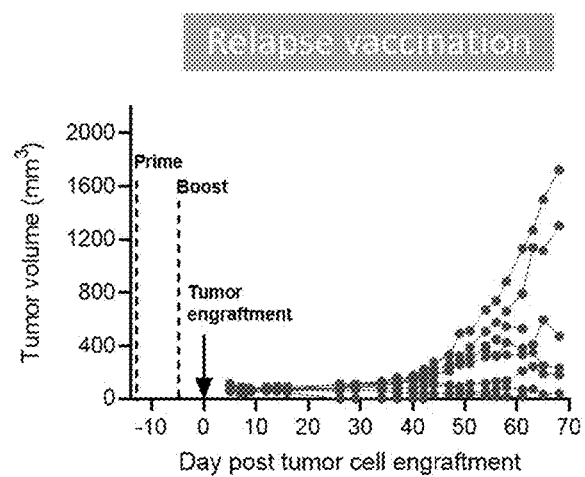
FIG. 5B

| Response Score[1] | SKOV3 | | OV90 | |
|---|---|---|---|---|
| | OC patients[2] | Healthy donors | OC patients[2] | Healthy donors |
| +++ | 5/8 | 1/7 | 1/8 | 0/7 |
| ++ | 0/8 | 2/7 | 0/8 | 0/7 |
| + | 1/8 | 1/7 | 4/8 | 2/7 |
| Total positive responders | 6/8 | 4/7 | 5/8 | 2/7 |

USE OF LEUKEMIA-DERIVED CELLS IN OVARIAN CANCER VACCINES

RELATED APPLICATIONS

This application claims priority to U.S. Provisional Patent Application Ser. No. 63/046,520, filed Jun. 30, 2020, and 63/111,390, filed Nov. 9, 2020, the entire disclosures of which are hereby incorporated by reference herein.

BACKGROUND

Ovarian cancer (OC) represents the second most common, and most lethal, gynecological malignancy. Within ovarian malignancies, epithelial ovarian cancer (EOC) represents 95% of all cases. Ovarian cancer is often diagnosed at a late stage resulting in a poor prognosis. About 75% of patients are diagnosed at late stage disease where the tumor has spread into the abdomen, and thereby the 5-year survival rates are mere 10-30%. While the survival rate of stage I patients is 90%, due to the lack of effective screening strategies and early detection markers, it is difficult to diagnose these patients.

First line treatment comprises debulking surgery and adjuvant or neoadjuvant chemotherapy. While advances in surgical procedures and chemotherapy regimens have moderately improved the survival rates in OC, most women are diagnosed at very late stage where the cure is unlikely. Despite first line treatment, many patients suffer from progressive ovarian cancer, an ovarian cancer that persists (e.g., recurs, or relapses) after an initial treatment for the ovarian cancer.

Ovarian cancer represents a challenge to current immuno-oncology approaches: the presence of tumor infiltrating lymphocytes correlates with increased patient survival in EOC; ovarian cancer is characterized by a strong immunosuppressive tumor microenvironment (MDSC, TAM, Treg); and ovarian cancer has poor responsiveness to immune checkpoint inhibitors.

Hence, there is a need in the art for novel immunotherapeutic approaches to treat ovarian cancer. In particular, there is a need for novel approaches to treat progressive ovarian cancer.

SUMMARY

The present disclosure is based, at least in part, on the finding that certain leukemia-derived cells (e.g., allogeneic leukemia-derived cells) are effective when administered as a vaccine for the treatment of a progressive ovarian cancer. DCP-001 is a vaccine derived from the DCOne leukemic cell line, DCOne cells of which can adopt a highly immunogenic mature dendric cell (mDC) phenotype. DCOne cells express multiple common tumor-associated antigens. DCOne mDC combine the DCOne tumor-associated antigen repertoire with a mDC costimulatory profile and form the basis for DCP-001, a frozen, irradiated product. DCP-001 has demonstrated promising signs of efficacy combined with a benign safety profile in a Ph I study in AML and is currently tested as a relapse vaccine in a Ph II study. Described herein are immunogenic compositions comprising an allogeneic leukemia-derived cell (e.g., DCP-001) for use in the treatment of ovarian cancer.

In one aspect, a method of treating a progressive ovarian cancer in a subject in need thereof, comprising: selecting a subject having had an initial treatment for the ovarian cancer; and administering to the subject an effective amount of an immunogenic composition comprising an allogeneic leukemia-derived cell is provided.

In certain exemplary embodiments, the administering is performed prior to the subject developing relapse or recurrence of the ovarian cancer.

In certain exemplary embodiments, the administering is performed within about two weeks to about six months after the initial treatment for the ovarian cancer. In certain exemplary embodiments, the administering is performed within about two weeks to about one month after the initial treatment for the ovarian cancer. In certain exemplary embodiments, the administering is performed about four weeks after the initial treatment for the ovarian cancer.

In certain exemplary embodiments, the administering is performed when the subject has exhibited an objective response following the initial treatment for the ovarian cancer. In certain exemplary embodiments, the objective response following the initial treatment is a complete response or a partial response. In certain exemplary embodiments, the administering is performed when the subject suffers from recurrent cancer.

In certain exemplary embodiments, the subject comprises an elevated serum level of one or more markers selected from the group consisting of CA-125, transferrin, transthyretin, apolipoprotein A1 (apoA1), beta-2 microglobulin (β2M), human epididymis protein 4 (HE4), human chorionic gonadotropin (HCG), alpha-fetoprotein (AFP), lactate dehydrogenase (LDH), inhibin, estrogen, testosterone, and any combination thereof.

In certain exemplary embodiments, the allogeneic leukemia-derived cell expresses at least one tumor associated antigen selected from the group consisting of WT-1, MUC-1, RHAMM, PRAME, p53, and Survivin. In certain exemplary embodiments, the allogeneic leukemia-derived cell expresses WT-1, MUC-1, PRAME, and Survivin. In certain exemplary embodiments, the allogeneic leukemia-derived cell comprises a dendritic cell phenotype. In certain exemplary embodiments, the allogeneic leukemia-derived cell comprises a mature dendritic cell phenotype. In certain exemplary embodiments, the allogeneic leukemia-derived cell comprises a genetic aberration between chromosome 11p15.5 to 11p12. In certain exemplary embodiments, the genetic aberration encompasses about 16 Mb of genomic regions. In certain exemplary embodiments, the allogeneic leukemia-derived cell is CD34-positive, CD1a-positive, and CD83-positive. In certain exemplary embodiments, the allogeneic leukemia-derived cell expresses a cell surface marker selected from the group consisting of CD14, DC-SIGN, Langerin, CD80, CD86, CD70, CD40, and any combination thereof. In certain exemplary embodiments, the allogeneic leukemia-derived cell is derived from the DCOne cell line. In certain exemplary embodiments, the allogeneic leukemia-derived cell has been inactivated. In certain exemplary embodiments, the allogeneic leukemia-derived cell has been inactivated via irradiation.

In certain exemplary embodiments, the immunogenic composition further comprises a pharmaceutically acceptable carrier. In certain exemplary embodiments, the immunogenic composition is formulated for intradermal administration. In certain exemplary embodiments, the administration is intradermal. In certain exemplary embodiments, the immunogenic composition is formulated for intraperitoneal administration. In certain exemplary embodiments, the administration is intraperitoneal. In certain exemplary embodiments, the immunogenic composition is formulated for intratumoral administration. In certain exemplary embodiments, the administration is intratumoral.

In certain exemplary embodiments, the method comprises administering to the subject at least one dose of the immunogenic composition. In certain exemplary embodiments, the method comprises administering to the subject four doses of the immunogenic composition, wherein each of the four doses comprises about 25 million allogeneic leukemia-derived cells. In certain exemplary embodiments, the method further comprises administering to the subject two doses of the immunogenic composition, wherein each of the two doses comprise about 10 million allogeneic leukemia-derived cells.

In certain exemplary embodiments, the ovarian cancer is a high grade serous ovarian cancer.

In certain exemplary embodiments, the initial treatment comprises chemotherapy and/or debulking surgery. In certain exemplary embodiments, the initial treatment comprises primary debulking surgery combined with adjuvant chemotherapy. In certain exemplary embodiments, the initial treatment comprises primary debulking surgery combined with six cycles of adjuvant chemotherapy. In certain exemplary embodiments, the initial treatment comprises neoadjuvant chemotherapy and interval debulking surgery. In certain exemplary embodiments, the initial treatment comprises three cycles of neoadjuvant chemotherapy and interval debulking surgery. In certain exemplary embodiments, the initial treatment further comprises three cycles of adjuvant chemotherapy. In certain exemplary embodiments, the chemotherapy comprises administration of carboplatin and/or paclitaxel.

In another aspect, a method of treating a progressive ovarian cancer in a subject in need thereof, comprising: administering to the subject an effective amount of an immunogenic composition comprising an allogeneic leukemia-derived cell is provided.

In certain exemplary embodiments, the subject has had an initial treatment for the ovarian cancer.

In certain exemplary embodiments, the administering is performed prior to the subject developing relapse or recurrence of the ovarian cancer.

In certain exemplary embodiments, the administering is performed within about two weeks to about six months after the initial treatment for the ovarian cancer. In certain exemplary embodiments, the administering is performed within about two weeks to about one month after the initial treatment for the ovarian cancer. In certain exemplary embodiments, the administering is performed about four weeks after the initial treatment for the ovarian cancer.

In certain exemplary embodiments, the administering is performed when the subject has exhibited an objective response following the initial treatment for the ovarian cancer. In certain exemplary embodiments, the objective response following the initial treatment is a complete response or a partial response. In certain exemplary embodiments, the administering is performed when the subject suffers from recurrent cancer.

In certain exemplary embodiments, the subject comprises an elevated serum level of one or more markers selected from the group consisting of CA-125, transferrin, transthyretin, apolipoprotein A1 (apoA1), beta-2 microglobulin (β2M), human epididymis protein 4 (HE4), human chorionic gonadotropin (HCG), alpha-fetoprotein (AFP), lactate dehydrogenase (LDH), inhibin, estrogen, testosterone, and any combination thereof.

In certain exemplary embodiments, the allogeneic leukemia-derived cell expresses at least one tumor associated antigen selected from the group consisting of WT-1, MUC-1, RHAMM, PRAME, p53, and Survivin. In certain exemplary embodiments, the allogeneic leukemia-derived cell expresses WT-1, MUC-1, PRAME, and Survivin. In certain exemplary embodiments, the allogeneic leukemia-derived cell comprises a dendritic cell phenotype. In certain exemplary embodiments, the allogeneic leukemia-derived cell comprises a mature dendritic cell phenotype. In certain exemplary embodiments, the allogeneic leukemia-derived cell comprises a genetic aberration between chromosome 11p15.5 to 11p12. In certain exemplary embodiments, the genetic aberration encompasses about 16 Mb of genomic regions. In certain exemplary embodiments, the allogeneic leukemia-derived cell is CD34-positive, CD1a-positive, and CD83-positive. In certain exemplary embodiments, the allogeneic leukemia-derived cell expresses a cell surface marker selected from the group consisting of CD14, DC-SIGN, Langerin, CD80, CD86, CD70, CD40, and any combination thereof. In certain exemplary embodiments, the allogeneic leukemia-derived cell is derived from the DCOne cell line. In certain exemplary embodiments, the allogeneic leukemia-derived cell has been inactivated. In certain exemplary embodiments, the allogeneic leukemia-derived cell has been inactivated via irradiation.

In certain exemplary embodiments, the method comprises administering to the subject at least one dose of the immunogenic composition. In certain exemplary embodiments, the method comprises administering to the subject four doses of the immunogenic composition, wherein each of the four doses comprises about 25 million allogeneic leukemia-derived cells. In certain exemplary embodiments, the method further comprises administering to the subject two doses of the immunogenic composition, wherein each of the two doses comprise about 10 million allogeneic leukemia-derived cells.

In certain exemplary embodiments, the ovarian cancer is a high grade serous ovarian cancer.

In certain exemplary embodiments, the administering is performed following an initial treatment of the ovarian cancer. In certain exemplary embodiments, the initial treatment comprises chemotherapy and/or debulking surgery. In certain exemplary embodiments, the initial treatment comprises primary debulking surgery combined with adjuvant chemotherapy. In certain exemplary embodiments, the initial treatment comprises primary debulking surgery combined with six cycles of adjuvant chemotherapy. In certain exemplary embodiments, the initial treatment comprises neoadjuvant chemotherapy and interval debulking surgery. In certain exemplary embodiments, the initial treatment comprises three cycles of neoadjuvant chemotherapy and interval debulking surgery. In certain exemplary embodiments, the initial treatment further comprises three cycles of adjuvant chemotherapy. In certain exemplary embodiments, the chemotherapy comprises administration of carboplatin and/or paclitaxel.

In certain exemplary embodiments, the immunogenic composition further comprises a pharmaceutically acceptable carrier. In certain exemplary embodiments, the immunogenic composition is formulated for intradermal administration. In certain exemplary embodiments, the administration is intradermal. In certain exemplary embodiments, the immunogenic composition is formulated for intraperitoneal administration. In certain exemplary embodiments, the administration is intraperitoneal. In certain exemplary embodiments, the immunogenic composition is formulated for intratumoral administration. In certain exemplary embodiments, the administration is intratumoral. In certain exemplary embodiments, the immunogenic composition is formulated for loco-regional lymph node administration. In certain exemplary embodiments, the administration is into a loco-regional lymph node.

In certain exemplary embodiments, the administering is performed during an initial treatment of the ovarian cancer. In certain exemplary embodiments, the initial treatment comprises surgery.

In certain exemplary embodiments, the immunogenic composition is formulated for loco-regional lymph node administration. In certain exemplary embodiments, the administration is into a loco-regional lymph node.

In certain exemplary embodiments, the method further comprises administering to the subject an effective amount of an immune checkpoint inhibitor. In certain exemplary embodiments, the immune checkpoint inhibitor is an antibody selected from the group consisting of anti-CTLA-4, anti-PD-1, anti-PD-L1, anti-CD47, anti-NKG2A, anti-B7-H3, and anti-B7-H4. In certain exemplary embodiments, the antibody is selected from the group consisting of ipilimumab, pembrolizumab, nivolumab, atezolizumab, avelumab, durvalumab, and cemiplimab.

In certain exemplary embodiments, the method further comprises administering to the subject an effective amount of an anti-angiogenesis therapy. In certain exemplary embodiments, the anti-angiogenesis therapy comprises an anti-angiogenesis agent selected from the group consisting of bevacizumab, aflibercept, sunitinib, and sorafenib.

In certain exemplary embodiments, the method further comprises administering to the subject an effective amount of a poly (ADP-ribose) polymerase (PARP) inhibitor therapy. In certain exemplary embodiments, the PARP inhibitor therapy comprises a PARP inhibitor selected from the group consisting of olaparib, niraparib, rucaparib, and veliparib.

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 1A shows the response of PRAME T cell clones to DCP-001; FIG. 1B shows the response of WT-1 T cell clones to DCP-001; FIG. 1C shows the response of MUC-1 T cell clones to DCP-001; and FIG. 1D shows the response of RHAMM T cell clones to DCP-001.

FIG. 4 depicts a schematic showing a vaccination strategy of an SKOV3 engrafted ovarian cancer mouse model, according to one embodiment.

FIG. 5A-FIG. 5D depict graphs showing the tumor volume (in mm$^3$) measured over time in SKOV3 tumor engrafted mice administered control vaccination (PBS; FIG. 5A); or relapse vaccination (FIG. 5B). FIG. 5C depicts a graph showing the mean tumor volume (in mm$^3$) per group measured over time in SKOV3 tumor engrafted mice administered control vaccination (PBS) or relapse vaccination. FIG. 5D depicts a graph showing the average tumor growth rate from 5 days after tumor engraftment until end of the study.

DETAILED DESCRIPTION

Figure 1A:
FIG. 1A-FIG. 1D depict plots demonstrating the response of antigen specific T cell clones against antigens expressed by DCOne mDCs (DCP001).
Figure 1A:
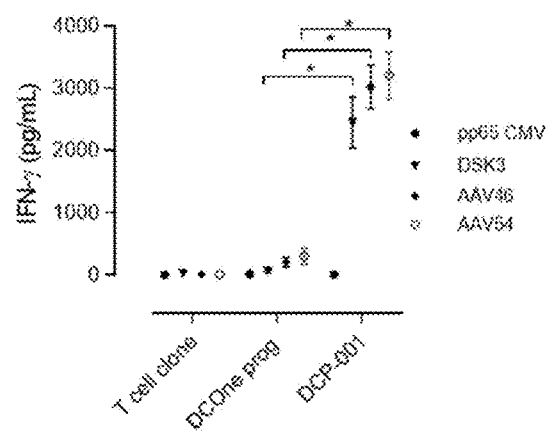

Methods for enhancing the effect of immune cells (e.g., genetically modified immune cells) in vivo is provided. In particular, methods of treating a disease or disorder are provided in which an inactivated modified cell of leukemic origin is administered to a subject who has undergone adoptive cell therapy with said modified immune. Such methods may prolong the duration of the clinical effect of a genetically modified immune cell, and/or function to stabilize subjects following adoptive cell therapy. In certain embodiments, the modified cell of leukemic origin is inactivated (e.g., via irradiation). In certain embodiments, the inactivated modified cell of leukemic origin is an irradiated DCOne derived cell.

It is to be understood that the methods described herein are not limited to particular methods and experimental conditions disclosed herein as such methods and conditions may vary. It is also to be understood that the terminology used herein is for the purpose of describing particular embodiments only, and is not intended to be limiting. The methods described herein use conventional molecular and cellular biological and immunological techniques that are well within the skill of the ordinary artisan. Such techniques are well known to the skilled artisan and are explained in the scientific literature.

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, e.g., ±5%, e.g., 1%, and e.g., ±0.1% from the specified value, as such variations are appropriate to perform the disclosed methods.

As used herein, to "alleviate" a disease means reducing the severity of one or more symptoms of the disease.

As used herein, the term "autologous" is meant to refer to any material derived from the same individual to which it is later to be re-introduced into the individual. As used herein, the term "allogeneic" refers to the involvement of living tissues or cells that are genetically dissimilar and hence immunologically incompatible, with respect to a subject in need of treatment. While genetically dissimilar, an allogeneic cell, e.g., an allogeneic leukemia-derived cell described herein, is derived from the same species. For example, a method described herein comprising administering to a subject an allogeneic leukemia-derived cell, refers to the administration of an leukemia-derived cell that is genetically dissimilar to the subject, albeit still of the same species.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the disclosure. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

As used herein "endogenous" refers to any material from or produced inside an organism, cell, tissue or system.

"Parenteral" administration of an immunogenic composition includes, e.g., subcutaneous (s.c.), intravenous (i.v.), intramuscular (i.m.), or intrasternal injection, or infusion techniques.

The term "subject," as used herein, refers to the recipient of a method as described herein, i.e., a recipient that can mount a cellular immune response, and is a mammal. In certain embodiments, the subject is a human. In certain embodiments, the subject is a domesticated animal, e.g., a horse, a cow, a pig, a sheep, a dog, a cat, etc. The terms "patient" and "subject" may be used interchangeably. In certain embodiments, the subject is a human suffering from a tumor (e.g., a solid tumor). In certain embodiments, the subject is a domesticated animal suffering from a tumor (e.g., a solid tumor).

The term "therapeutic" as used herein means a treatment and/or prophylaxis. A therapeutic effect is obtained by suppression, remission, or eradication of a disease state.

To "treat" a disease as the term is used herein, means to reduce the frequency or severity of at least one sign or symptom of a disease or disorder experienced by a subject.

The term "tumor," as used herein, includes reference to cellular material, e.g., a tissue, proliferating at an abnormally high rate. A growth comprising neoplastic cells is a neoplasm, also known as a "tumor," and generally forms a distinct tissue mass in a body of a subject. A tumor may show partial or total lack of structural organization and functional coordination with the normal tissue. As used herein, a tumor is intended to encompass hematopoietic tumors as well as solid tumors. In certain embodiments, the tumor is a solid tumor. The term "tumor," as used herein, includes reference to the tumor micro-environment or tumor site, i.e., the area within the tumor and the area directly outside the tumorous tissue. In certain embodiments, the tumor micro-environment or tumor site includes an area within the boundaries of the tumor tissue. In certain embodiments, the tumor micro-environment or tumor site includes the tumor interstitial compartment of a tumor, which is defined herein as all that is interposed between the plasma membrane of neoplastic cells and the vascular wall of the newly formed neovessels. As used herein, the terms "tumor micro-environment" or "tumor site" refers to a location within a subject in which a tumor resides, including the area immediately surrounding the tumor.

In certain exemplary embodiments, the tumor is an ovarian cancer (e.g., an epithelial ovarian cancer (EOC), which can be further subtyped into a serous, a clear cell, an endometrioid, a mucinous, or a mixed epithelial ovarian cancer). As used herein, "ovarian cancer" refers to a cancer that forms in tissues of or near the ovary.

About 85% to 90% of malignant ovarian cancers are EOCs. EOCs have several features that can be used to classify epithelial ovarian carcinomas into different types. The serous type is by far the most common, and can include high grade and low grade tumors. The other main types include mucinous, endometrioid, and clear cell (serous carcinomas (52%), clear cell carcinoma (6%), mucinous carcinoma (6%), endometrioid carcinoma (10%)).

Epithelial ovarian tumors typically start from the cells that cover the outer surface of the ovary. Most ovarian tumors are epithelial cell tumors. Germ cell tumors typically start from the cells that produce the ova. Stromal ovarian tumors typically start from structural tissue cells that hold the ovary together and produce the female hormones estrogen and progesterone. Ovarian tumors can be classified as benign, borderline (i.e., low malignant potential), or malignant.

The assignment of a tumor grade, based on the apparent degree of cytological aberration, allows for an additional degree of stratification for serous and endometrioid EOCs. Thus, despite sharing some similarity in histological appearance and terminology, high-grade and low-grade serous carcinomas of the ovary are considered to be two different neoplasms, with distinct modes of carcinogenesis, molecular genetic features and sites of origin.

In the most common type of ovarian cancer, high grade serous ovarian cancer (HGSOC), the tumors are simply divided into low grade and high grade and a grading number is not given. There is a low grade serous counterpart, which is less common. All other ovarian cancers are graded as 1, 2 and 3. Grade 1 (well differentiated) cancers have cells that closely resemble normal cells and are less likely to spread or recur. Grade 2 (moderately differentiated) cancers and grade 3 (poorly differentiated) cancers show increasing abnormality of appearance compared to normal cells. They are also increasingly more likely to spread and recur.

EOCs may be subtyped into two broad categories called Type 1 and Type 2. (For a review, see Lisio et al. (2019) *Int. J. Mol. Sci.* 20(4): 952, incorporated herein by reference for all purposes.) The Type 1 neoplasms typically develop along a step-wise progression from pre-malignant or borderline lesions in a manner common to many other epithelial cancers. From the genetic perspective, these tumors display frequent oncogenic alterations to many cellular signalling pathways such as RAS-MAPK and PI3K-AKT but are otherwise genomically stable and p53 wild type. From a clinical perspective, these tumors typically present as large, unilateral, cystic neoplasms that grow in an indolent fashion and when confined to the ovary they have an excellent prognosis. This category includes low grade serous, clear-cell, mucinous and transitional cell (Brenner) subtypes.

By contrast, the Type 2 category is marked by a far more aggressive pattern of disease behavior. Type 2 tumors develop rapidly and usually are disseminated widely at the time of presentation, resulting in poor overall prognosis. From a genetic viewpoint, these tumors are characterized by p53 mutations and genomic instability due to defects in pathways contributing to DNA repair. The prototypical Type 2 neoplasm, high grade serous ovarian cancer (HGSOC), is by far the dominant subtype diagnosed clinically and accounts for 70-80% of deaths from all forms of ovarian cancer.

HGSOC is a unique type of epithelial cancer that is characterized by nearly universal mutation in and dysfunction of p53, genomic instability rather than driver mutations, advanced stage at onset, and probable fallopian tube epithelium origin, with a serous tubal in situ carcinoma precursor. (See Kohn and Ivy (2017) *Am. Soc. Clin. Oncol. Educ. Book* 37: 443, incorporated herein by reference in its entirety.) Germline deleterious mutations in BRCA1 and BRCA2, as well as other less prevalent genes involved in DNA repair, such as PALB2 and RAD51c, are associated with its carcinogenesis and may predict susceptibility to classes of treatment agents, including DNA-damaging agents and DNA repair inhibitors. Loss of function of these genes is associated with homologous recombination dysfunction (HRD). It is now recognized that there may be HGSOC with wild-type BRCA1 and BRCA2 with an identifiable HRD phenotype.

The term "immunogenic composition," as used herein, refers to a substance which induces a specific immune response against an immunogen in a subject who is in need of an immune response against said immunogen. The composition may include an adjuvant and optionally one or more pharmaceutically-acceptable carriers, excipients and/or diluents. The immunogenic composition comprises an allogeneic leukemia-derived cell.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Allogeneic Leukemia-Derived Cells

Provided herein are methods comprising the use of a leukemia-derived cell. As used herein, the term "leukemia-derived cell" refers to a cell of leukemic origin that is capable of presenting an antigen, or an immunogenic portion thereof, together with an MHC class I complex or MHC class II complex. The term "allogeneic leukemia-derived cell" refers to a leukemia-derived cell that is genetically dissimilar with respect to the subject it is utilized to treat, yet is of the same species. In some embodiments, an allogeneic leukemia-derived cell provided herein comprises a dendritic cell phenotype. In some embodiments, an allogeneic leukemia-derived cell provided herein comprises a mature dendritic cell phenotype. The term "dendritic cell," as used herein, refers to a professional antigen presenting cell (APC) that can take up an antigen, and is capable of presenting the antigen, or an immunogenic portion thereof, together with an MHC class I complex or MHC class II complex. In some embodiments, an allogeneic leukemia-derived cell as described herein has a mature dendritic cell phenotype capable of performing similar functions to those of a mature dendritic cell. The term dendritic cell includes both immature dendritic cells ("imDC") and mature dendritic cells ("mDC"), depending on maturity. In certain embodiments, the allogeneic leukemia-derived cell is a cell derived from cell line DCOne as deposited under the conditions of the Budapest treaty with the DSMZ under accession number DSMZ ACC3189 on 15 Nov. 2012. The process of obtaining mature cells from the deposited DCOne cell line is for instance described in EP2931878B1, the disclosure of which is incorporated by reference herein in its entirety.

In certain embodiments, the allogeneic leukemia-derived cell is derived from a leukemia cell. In certain embodiments, the allogeneic leukemia-derived cell is derived from a subject having leukemia (e.g., a genetically dissimilar subject with respect to the subject that the leukemia-derived cell is utilized to treat). In certain embodiments, the allogeneic leukemia-derived cell is derived from the peripheral blood of a patient having leukemia. In certain embodiments, the allogeneic leukemia-derived cell is derived from the peripheral blood of a patient having acute myeloid leukemia. The skilled artisan will recognize that an allogeneic leukemia-derived cell can be derived from any patient-obtained peripheral blood, wherein the patient has any type of leukemia, given that the leukemia-derived cell thus derived comprises the characteristics disclosed herein.

In certain embodiments, the allogeneic leukemia-derived cell is CD34-positive, CD1a-positive, and CD83-positive. In certain embodiments, the allogeneic leukemia-derived cell comprises a cell surface marker selected from the group consisting of CD14, DC-SIGN, Langerin, CD40, CD70, CD80, CD83, CD86, and any combination thereof. In certain embodiments, the allogeneic leukemia-derived cell expresses a cell surface marker selected from the group consisting of CD14, DC-SIGN, Langerin, CD40, CD70, CD80, CD83, CD86, and any combination thereof. In certain embodiments, the allogeneic leukemia-derived cell comprises an MHC class I molecule. In certain embodiments, the allogeneic leukemia-derived cell comprises an MHC class II molecule.

In certain embodiments, the allogeneic leukemia-derived cell comprises a genetic aberration between chromosome 11p15.5 to 11p12. In certain embodiments, the genetic aberration encompasses about 16 Mb of genomic regions (e.g., from about 20.7 Mb to about 36.6 Mb). In certain embodiments, the genetic aberration contains a loss of about 60 known and unknown genes.

In certain embodiments, the allogeneic leukemia-derived cell comprises a co-stimulatory molecule. In certain embodiments, the co-stimulatory molecule includes, without limitation, an MHC class I molecule, BTLA and Toll ligand receptor. Examples of co-stimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In certain embodiments, the allogeneic leukemia-derived cell comprises at least one endogenous antigen. Depending on the leukemic origin of the leukemia-derived cell, the leukemia-derived cell may comprise at least one known endogenous antigen that is specific to the leukemic origin. In certain embodiments, the endogenous antigen is a tumor-associated antigen. In certain embodiments, the endogenous tumor-associated antigen may be selected from the group consisting of WT-1, RHAMM, PRAME, p53, Survivin, and MUC-1.

In certain embodiments, the allogeneic leukemia-derived cell of the present disclosure is a cell of cell line DCOne as described in PCT Publication Nos. WO 2014/006058 and WO 2014/090795, the disclosures of which are incorporated by reference herein in their entireties. In certain embodiments, an allogeneic leukemia-derived cell of the present disclosure is a cell of cell line DCOne and comprises a mature dendritic cell phenotype that is CD34-positive, CD1a-positive, and CD83-positive. In certain embodiments, the allogeneic leukemia-derived cell is a cell of cell line DCOne and is CD34-positive, CD1a-positive, and CD83-positive. In certain embodiments, the allogeneic leukemia-derived cell is a cell of cell line DCOne and comprises a cell surface marker selected from the group consisting of CD14, DC-SIGN, Langerin, CD80, CD86, CD40, CD70, and any combination thereof. In certain embodiments, the allogeneic leukemia-derived cell is a cell of cell line DCOne and comprises MHC class I. In certain embodiments, the allogeneic leukemia-derived cell is a cell of cell line DCOne and comprises MHC class II. In certain embodiments, the allogeneic leukemia-derived cell is a cell of cell line DCOne and comprises a genetic aberration between chromosome 11p15.5 to 11p12. In certain embodiments, the allogeneic leukemia-derived cell is a cell of cell line DCOne and comprises a genetic aberration that encompasses about 16 Mb of genomic regions (e.g., from about 20.7 Mb to about 36.6 Mb). In certain embodiments, the allogeneic leukemia-derived cell is a cell of cell line DCOne and comprises a genetic aberration that contains a loss of about 60 known and unknown genes.

As provided herein, certain methods utilize the use of an allogeneic leukemia-derived cell, wherein the allogeneic leukemia-derived cell is inactivated. Various methods of inactivating an allogeneic leukemia-derived cell of the present disclosure are known to those of skill in the art. In certain embodiments, the allogeneic leukemia-derived cell is irradiated. In certain embodiments, the allogeneic leukemia-derived cell is irradiated prior to its use in a method disclosed herein. Irradiation can, for example, be achieved by gamma irradiation at 30-150 Gy, e.g., 100 Gy, for a period of 1 to 3 hours, using a standard irradiation device (Gammacell or equivalent). Irradiation ensures that any remaining progenitor cell in a composition comprising the allogeneic leukemia-derived cell, e.g., a CD34 positive cell, cannot continue dividing. The cells may, for example, be irradiated prior to injection into patients, when used as a vaccine, or immediately after cultivating is stopped.

C. Methods of Treatment

Provided herein are methods for treating a progressive ovarian cancer in a subject. As used herein, a "progressive ovarian cancer" refers to an ovarian cancer that persists (e.g., recurs, or relapses) after an initial treatment for the ovarian cancer. In certain embodiments, a method for treating a progressive ovarian cancer in a subject comprises administering to the subject an effective amount of an immunogenic composition comprising an allogeneic leukemia-derived cell described herein. In certain embodiments, a method for treating a progressive ovarian cancer in a subject comprises: (1) selecting a subject having had an initial treatment for the ovarian cancer; and (2) administering to the subject an effective amount of an immunogenic composition comprising an allogeneic leukemia-derived cell described herein.

As used herein, the terms "subject" or "individual" or "patient," are used interchangeably herein, and refers to any subject, particularly a mammalian subject, for whom diagnosis or therapy is desired. Mammalian subjects include for example, humans, domestic animals, farm animals, and zoo, sports, or pet animals such as dogs, cats, guinea pigs, rabbits, rats, mice, horses, cattle, and cows.

As used herein, the terms "treat" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to or at risk of having the condition or disorder or those in which the condition or disorder is to be prevented. In certain embodiments, treatment also refers to preventing recurrence and delaying recurrence of a disease or disorder, e.g., a progressive ovarian cancer.

As used herein, an "effective amount" is an amount sufficient to effect beneficial or desired results, e.g., such as an effective amount of nucleic acid transfer and/or expression, expression of a desired effector molecule(s) (e.g., cytokine), and/or the attainment of a desired therapeutic endpoint (e.g., partial or full reduction in size of a tumor). An effective amount can be administered in one or more administrations, applications or dosages. In one aspect, an effective amount of a polycistronic nucleic acid construct is an amount sufficient to transform/transduce/transfect at least one cell in a population of cells comprising at least two cells.

As used herein, a "therapeutically effective amount" is used to mean an amount sufficient to prevent, correct and/or normalize an abnormal physiological response or a measurable improvement in a desirable response (e.g., enhanced adaptive immune response). In one aspect, a "therapeutically effective amount" is an amount sufficient to reduce by at least about 30%, at least 50% at least 70%, at least 80%, or at least 90%, a clinically significant feature of pathology, such as for example, size of a tumor mass.

Subjects that would benefit from a method of treating a progressive ovarian cancer provided herein include those that have ovarian cancer, e.g., a progressive ovarian cancer. Also suitable are subjects that have previously had an initial treatment for ovarian cancer. In certain embodiments, the initial treatment comprises standard of care treatment for the progressive ovarian cancer. Standard of care for ovarian cancer includes surgery, chemotherapy and/or radiation therapy. In certain embodiments, the initial treatment comprises debulking surgery. In certain embodiments, the initial treatment comprises chemotherapy and debulking surgery.

Surgery is the main treatment for ovarian cancer and is an option for subjects where the vast majority of the cancer or affected tissue can be successfully removed. Early-stage ovarian cancer patients may be eligible for minimally-invasive procedures to remove ovarian tumors to preserve fertility. Other ovarian cancer surgical procedures include removal of, without limitation, the uterus and/or cervix (i.e., partial or total hysterectomy), the ovaries and fallopian tubes (unilateral or bilateral salpingo-oophorectomy), the omentum (i.e., omentectomy), and/or nearby lymph nodes. Tissue from the pelvis, abdomen, colon, bladder, stomach, liver spleen, appendix, pancreas and/or fluid in the abdomen may be removed depending on the extent of the cancer, and samples may be taken for analysis to determine the presence and/or extent of the cancer. In certain embodiments, the initial treatment comprises debulking surgery. As used herein, the term "debulking surgery" refers to the removal of as much of a tumor as possible. Debulking may increase the chance that chemotherapy or radiation therapy will kill all the tumor cells. Debulking surgery may also be performed to relieve symptoms or help the subject live longer. As such, a method of treating a progressive ovarian cancer described herein comprises selecting a subject having had an initial treatment for the ovarian cancer, wherein the initial treatment comprises debulking surgery.

Standard of care for the treatment of ovarian cancer includes chemotherapy. Chemotherapy can be utilized in the adjuvant or neoadjuvant setting. Adjuvant chemotherapy is often given to a subject after the primary treatment. For example, primary debulking surgery is often accompanied by adjuvant chemotherapy. Neoadjuvant chemotherapy occurs when the chemotherapy is given before the main treatment. In certain embodiments, neoadjuvant chemotherapy may allow for the monitoring of any changes to the tumor in response to chemotherapy prior to surgery. In certain embodiments, adjuvant and neoadjuvant chemotherapy includes, without limitation, intravenous chemotherapy, where the chemotherapy is administered by infusion; intraperitoneal chemotherapy, where the chemotherapy is administered directly into the abdominal cavity; and consolidation chemotherapy, where the subject is given additional chemotherapy after adjuvant treatment.

The cancer stage at diagnosis and extent of surgical cytoreduction determine the chemotherapeutic treatment duration and route. The type of first line treatment will depend on the cancer to be treated and on the stage of the cancer. Several staging systems are known to those of skill in the art, e.g., the tumor/lymph nodes/metastasis (TNM) staging system, or FIGO staging for ovarian cancer. As such, in some embodiments, it is critical that subjects receive comprehensive surgical staging.

Numerous studies have shown the efficacy of the combination of a platinum agent and a taxane, e.g., paclitaxel, following initial debulking surgery, which has become the standard of care for the treatment of ovarian cancer. As used herein, a "taxane" refers to a compound class of diterpenes that feature a taxadiene core structure. Exemplary taxanes include, but are not limited to, paclitaxel, docetaxel and cabazitaxel. As used herein, a "platinum agent" refers to metal complex compound, wherein the platinum is the metal component. The platinum may for example be complexed by oxygen or nitrogen atoms of one or more organic or inorganic compounds to form the platinum complex. Exemplary platinum agents include, but are not limited to, carboplatin and cisplatin. As such, a method of treating a progressive ovarian cancer described herein comprises selecting a subject having had an initial treatment for the ovarian cancer, wherein the initial treatment comprises adjuvant or neoadjuvant chemotherapy. In certain embodiments, the adjuvant chemotherapy comprises administering to the subject a taxane and/or platinum agent. In certain embodiments, the taxane utilized in an adjuvant chemotherapy is paclitaxel. In certain embodiments, the platinum agent utilized in an adjuvant chemotherapy is carboplatin. Accordingly, in certain embodiments, the adjuvant chemotherapy comprises administering to the subject paclitaxel and/or carboplatin.

In cases where optimal debulking surgery is not feasible for a subject, e.g., subjects having comorbidities, poor performance status, or massive ascites, neoadjuvant chemotherapy followed by debulking surgery may be part of an initial treatment regimen. In certain embodiments, the neoadjuvant chemotherapy comprises administering to the subject a taxane and/or platinum agent. In certain embodiments, the taxane utilized in a neoadjuvant chemotherapy is paclitaxel. In certain embodiments, the platinum agent utilized in a neoadjuvant chemotherapy is carboplatin. Accordingly, in certain embodiments, the neoadjuvant chemotherapy comprises administering to the subject paclitaxel and/or carboplatin.

Effective intravenous treatment regimens of chemotherapy are known in the art, and include, for example, Paclitaxel 175 mg/m$^2$ intravenously (IV) over 3 hours followed by carboplatin area under the curve (AUC) 5-7.5 IV over 1 hour day 1, repeated every 3 weeks for 6 cycles; Docetaxel 60-75 mg/m$^2$ IV over 1 hour followed by carboplatin AUC 5-6 IV over 1 hour day 1, repeated every 3 weeks for 6 cycles; and Dose dense paclitaxel 80 mg/m$^2$ IV over 1 hour days 1, 8, and 15 and carboplatin AUC 6 IV over 1 hour day 1, repeated every 3 weeks for 6 cycles. Effective intraperitoneal treatment regimens of chemotherapy are also known in the art, and include, for example, Paclitaxel 135 mg/m$^2$ IV continuous infusion over 24 h day 1, cisplatin 75-100 mg/m$^2$ intraperitoneally (IP) day 2 after completion of IV paclitaxel, paclitaxel 60 mg/m$^2$ IP day 8, repeated every 3 weeks for 6 cycles; and Paclitaxel 135 mg/m$^2$ IV over 3 h day 1, cisplatin 75-100 mg/m$^2$ IP day 2, paclitaxel 60 mg/m$^2$ IP day 8, repeated every 3 weeks for 6 cycles.

In certain embodiments, a method for treating a progressive ovarian cancer in a subject comprises selecting a subject having had an initial treatment for the ovarian cancer, wherein the initial treatment comprises primary debulking surgery combined with adjuvant chemotherapy. In certain embodiments, the initial treatment comprises primary debulking surgery combined with six cycles of adjuvant chemotherapy. In certain embodiments, the initial treatment comprises neoadjuvant chemotherapy and interval debulking surgery. In certain embodiments, the initial treatment comprises three cycles of neoadjuvant chemotherapy and interval debulking surgery. In certain embodiments, the initial treatment further comprises three cycles of adjuvant chemotherapy.

In certain embodiments, the majority of subjects with advanced ovarian cancer achieve a complete clinical remission after cytoreductive surgery and combination chemotherapy, however, few will experience long-term remission. In such cases, the subject is said to be at risk for cancer relapse. In certain embodiments, a method for treating a progressive ovarian cancer in a subject described herein comprises administering to the subject an effective amount of an immunogenic composition comprising an allogeneic leukemia-derived cell described herein, wherein the administering is performed prior to the subject developing relapse for the ovarian cancer. In certain embodiments, a method for treating a progressive ovarian cancer in a subject described herein comprises administering to the subject an effective amount of an immunogenic composition comprising an allogeneic leukemia-derived cell described herein, wherein the administering is performed when the subject is in remission following the initial treatment for the ovarian cancer. In certain embodiments, a method for treating a progressive ovarian cancer in a subject described herein comprises administering to the subject an effective amount of an immunogenic composition comprising an allogeneic leukemia-derived cell described herein, wherein the administering is performed when the subject suffers from recurrent cancer (e.g., relapsed cancer).

In certain embodiments, a method for treating a progressive ovarian cancer in a subject described herein comprises administering to the subject an effective amount of an immunogenic composition comprising an allogeneic leukemia-derived cell described herein, wherein the administering is performed when the subject has exhibited an objective response following the initial treatment for the ovarian cancer. In certain embodiments, the objective response following the initial treatment is a complete response. As used herein, the term "complete response" refers to the disappearance of all signs of disease in a subject, in response to treatment. For example, a subject exhibits a complete response when all signs of cancer have disappeared in response to a treatment. A complete response does not necessarily mean that the cancer has been cured. In certain embodiments, the objective response following the initial treatment is a partial response. As used herein, the term "partial response" refers to a reduction or decrease of a disease in a subject. For example, for a subject having cancer, a partial response may refer to a decrease in the size of a tumor, or in the extent of cancer in the body, in response to a treatment.

Methods of diagnosis and monitoring of ovarian cancer are known in the art. In some embodiments, ovarian cancer can be diagnosed and/or monitored using biomarker analysis. In certain embodiments, a subject having a progressive ovarian cancer comprises an elevated serum level of one or more biomarkers associated with ovarian cancer. For example, biomarkers useful in selecting a patient for a method described herein, include, without limitation, cancer antigen 125, also known as CA-125 or MUC-16; transferrin; transthyretin; apolipoprotein A1 (apoA1); beta-2 microglobulin (P2M); human epididymis protein 4 (HE4); human chorionic gonadotropin (HCG); alpha-fetoprotein (AFP); lactate dehydrogenase (LDH); inhibin; estrogen; and testosterone. In certain embodiments, a subject suffering from recurrent cancer can be identified by analyzing one or more biomarkers selected from the group consisting of CA-125; transferrin; transthyretin; apolipoprotein A1 (apoA1); beta-2 microglobulin (P2M); human epididymis protein 4 (HE4); human chorionic gonadotropin (HCG); alpha-fetoprotein (AFP); lactate dehydrogenase (LDH); inhibin; estrogen; and testosterone. See, e.g., Hentze et al. *Contemporary Clin. Trials Comm.* (2017) 8:167-174, the disclosure of which is incorporated by reference herein in its entirety. In some embodiments, ovarian cancer can be detected by art-recognized assays, e.g., the multivariate index assay called OVA1, which evaluates serum concentrations of 5 different markers (CA-125-II, transferrin, transthyretin, apoA1, and P2M).

In certain embodiments, a subject suffering from recurrent cancer can be identified by the presence of one or more microlesions of the progressive ovarian cancer. Such microlesions can be detected using imaging technologies known in the art, for example, using ultrasound imaging, positron emission tomography-computer tomography (PET-CT) imagine, dynamic contrast-enhanced magnetic resonance imaging (MRI), diffusion-weighted MRI and perfusion CT. In certain embodiments, the one or more microlesions are detected by ultrasound imaging or computer tomography (CT) scan.

In some embodiments, the administering is performed within a suitable time after the initial treatment for the ovarian cancer. For example, in some embodiments, the administering is performed about one day, two days, three days, four days, five days, six days, seven days (one week), eight days, nine days, ten days, eleven days, twelve days, thirteen days, two weeks, three weeks, four weeks, five weeks, six weeks, seven weeks, eight weeks, and any interval therebetween after the initial treatment for the ovarian cancer. In some embodiments, the administering is performed within about, e.g., one week, two weeks, three weeks, four weeks, five weeks, six weeks, seven weeks, eight weeks, or any interval therebetween, after the initial treatment for the ovarian cancer. In certain embodiments, the administering is performed within about two weeks after the initial treatment for the ovarian cancer. In some embodiments, the administering is performed within about, e.g., one month, two months, three months, four months, five months, six months, seven months, eight months, or any interval therebetween, after the initial treatment for the ovarian cancer. In certain embodiments, the administering is performed within about one month after the initial treatment for the ovarian cancer. In certain embodiments, the administering is performed within about two weeks to about one month after the initial treatment for the ovarian cancer. In certain embodiments, the administering is performed about four weeks after the initial treatment for the ovarian cancer.

In some embodiments, a method for treating a progressive ovarian cancer provided herein comprises administering to a subject one or more doses of an effective amount of an immunogenic composition comprising an allogeneic leukemia-derived cell. In some embodiments, each dose of an immunogenic composition comprises from about 10 million to about 25 million allogeneic leukemia-derived cells (e.g., allogeneic leukemia-derived cells as described herein). For example, each dose of an immunogenic composition comprises about 1 million, about 2 million, about 3 million, about 4 million, about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 21 million, about 22 million, about 23 million, about 24 million, about 25 million, about 26 million, about 27 million, about 28 million, about 29 million, about 30 million, about 31 million, about 32 million, about 33 million, about 34 million, about 35 million allogeneic leukemia-derived cells. In some embodiments, each dose of the immunogenic composition comprises from about 1 million to about 35 million allogeneic leukemia-derived cells, or any interval therebetween. In certain embodiments, each dose of the immunogenic composition comprises about 10 million allogeneic leukemia-derived cells. In certain embodiments, each dose of an immunogenic composition comprises about 25 million allogeneic leukemia-derived cells.

In some embodiments, one or more doses of an immunogenic composition comprising an allogeneic leukemia-derived cell is administered to the subject. For example, one dose, two doses, three doses, four doses, five doses, six doses, seven doses, eight doses, nine doses, ten doses, eleven doses, twelve doses, or more of the immunogenic composition comprising an allogeneic leukemia-derived cell is administered to the subject. Each of the one or more doses may contain substantially the same number of allogeneic leukemia-derived cells, or may contain different numbers of allogeneic leukemia-derived cells. In certain embodiments, a method for treating a progressive ovarian cancer provided herein comprises administering to a subject at least one dose of an effective amount of an immunogenic composition comprising an allogeneic leukemia-derived cell. In certain embodiments, a method for treating a progressive ovarian cancer provided herein comprises administering to the subject four doses of the immunogenic composition, wherein each of the four doses comprises about 25 million allogeneic leukemia-derived cells. In certain embodiments, a method for treating a progressive ovarian cancer provided herein further comprises administering to the subject two doses of the immunogenic composition, wherein each of the two doses comprise about 10 million allogeneic leukemia-derived cells. As such, in certain embodiments, a subject receives at least six doses of the immunogenic composition, four doses each having about 25 million allogeneic leukemia-derived cells, and two doses each having about 10 million allogeneic leukemia-derived cells. Accordingly, in certain embodiments a subject is administered a total of about 120 million allogeneic leukemia-derived cells. In some embodiments, a subject is administered a total of from about 50 million to about 200 million allogeneic leukemia-derived cells, e.g., about 50 million cells, about 60 million cells, about 70 million cells, 80 million cells, about 90 million cells, about 100 million cells, about 110 million cells, about 120 million cells, about 130 million cells, about 140 million cells, about 150 million cells, about 160 million cells, about 170 million cells, about 180 million cells, about 190 million cells, about 200 million cells, or any number of cells therebetween.

In some embodiments, doses of the immunogenic compositions (i.e., comprising an allogeneic leukemia-derived cell) may be administered at an interval of time, e.g., at 1 week intervals, at 2 week intervals, at 3 week intervals, at 4 week intervals, at 5 week intervals, at 6 week intervals, at 7 week intervals, at 8 week intervals, at 9 week intervals, at 10 week intervals, at 11 week intervals, at 12 week intervals, or longer. In some embodiments, the time between doses is from about 1 day to about 21 days, from about 1 day to about 22 days, from about 1 day to about 23 days, from about 1 day to about 24 days, from about 1 day to about 3 weeks, from about 1 day to about 4 weeks, from about 1 day to about 5 weeks, from about 1 day to about 10 weeks, from about 1 day to about 15 weeks, from about 1 day to about 20 weeks, from about 1 day to about 25 weeks, from about 1 day to about 30 weeks, from about 1 day to about 35 weeks, from about 1 day to about 40 weeks, from about 1 day to about 45 weeks, from about 1 day to about 50 weeks, from about 1 day to about 1 year, and any intervening amount of time thereof. In some embodiments, the time between doses is about 1 day to about 1 month, 14 days to about 2 months, 1 month to about 3 months, 2 months to about 5 months, 4 months to about 6 months, 5 months to about 7 months, 6 months to about 8 months, 7 months to about 9 months, 8 months to about 10 months, 9 months to about 11 months, 10 months to about 12 months, 11 months to about 13 months, 12 months to about 14 months, 13 months to about 15 months, 14 months to about 16 months, 15 months to about 17 months, 16 months to about 18 months, 17 months to about 19 months, 18 months to about 20 months, 19 months to about 21 months, 20 months to about 22 months, 21 months to about 23 months, 22 months to about 24 months, 3 months to about 1 year, 6 months to about 1 year, and any intervening range of time thereof.

The methods provided herein are suitable for treating an ovarian cancer, e.g., a progressive ovarian cancer. Ovarian cancer can be of epithelial or non-epithelial origin. Epithelial origin ovarian cancer includes, e.g., high grade serous ovarian cancer, clear cell ovarian cancer, endometroid ovarian cancer, mucinous ovarian cancer, and low grade serous ovarian cancer. Non-epithelial origin ovarian cancer includes, e.g., germ cell tumors, stromal tumors such as granulosa cell tumor and Sertoli Leydig cell tumor. In certain embodiments, a method for treating a progressive ovarian cancer provided herein is useful for treating high grade serous ovarian cancer.

Methods for treating a progressive ovarian cancer described herein comprises administering to the subject an effective amount of an immunogenic composition comprising an allogeneic leukemia-derived cell. As described above, methods described herein include methods comprising the administration of one or more doses of the immunogenic composition. In some embodiments, the one or more doses are administered via the same route of delivery. In some embodiments, the one or more doses are administered via different routes of delivery.

In certain embodiments, an immunogenic composition is administered intratumorally or peri-tumorally. In such cases, the immunogenic composition is formulated for intratumoral administration. Intratumoral administration of an immunogenic composition includes direct administration of the immunogenic composition into a tumor, e.g., into the center of a tumor, or into any location within a tumor mass. Intratumoral administration also includes administration of the immunogenic composition proximal to a tumor, e.g., the space surrounding the tumor.

In certain embodiments, an immunogenic composition is administered extratumorally. In such cases, the immunogenic composition is formulated for the specific extratumoral administration. Extratumoral administration includes, e.g., parenteral administration, which includes intravenous, intra-arterial, subcutaneous, intradermal, intranodal, intralymphatic and intramuscular administration, which are all well known to the person skilled in the art. In certain embodiments, administration of an immunogenic composition described herein is delivered by a mode selected from the group consisting of intramuscular injection, subcutaneous injection, intravenous injection, intraarterial injection, intraperitoneal injection, intrasternal injection, intradermal injection, transcutaneous injection, transdermal injection, and delivery to the interstitial space of a tissue.

Extratumoral administration also includes administration to a site distal to a tumor site. For example, extratumoral administration includes administering an immunogenic composition at a site at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm, at least about 35 mm, at least about 40 mm, at least about 45 mm, at least about 50 mm, at least about 60 mm, at least about 70 mm, at least about 80 mm, at least about 90 mm, at least about 10 cm, at least about 20 cm, at least about 30 cm, at least about 40 cm, at least about 50 cm, 50 cm or more away from a tumor (e.g., the edge of a tumor, or the center of a tumor).

Extratumoral administration also includes administering an immunogenic composition at a site in an organ system that is different to the organ system in which a tumor resides. For example, if the tumor resides at or in an ovary (e.g., an epithelial ovarian cancer, a progressive ovarian cancer), the method comprises distally administering the immunogenic composition at a site in an organ system that is not the ovary, e.g., the liver, kidney, etc. The term "organ" or "organ system" as used herein refers to a group of tissues with similar functions. Examples of organ systems include, without limitation, the muscular system, the digestive system (e.g., stomach, small intestine, large intestine, liver, pancreas, etc.), the respiratory system (e.g., lungs), the urinary system (e.g., kidneys, bladder, etc.), the reproductive organs (e.g., male and female reproductive system, ovaries, placenta, prostate, etc.), the endocrine system, the circulatory system, the nervous system (e.g., central and peripheral nervous systems), and the integumentary system (e.g., skin, subcutaneous tissue).

Administration of an immunogenic composition may also be performed at a site contralateral to the tumor site. In certain embodiments, the method comprises administering an immunogenic composition at a site contralateral to a tumor site (a site in which the tumor resides). For example, if the tumor resides at or in an ovary, the method comprises distally administering an immunogenic composition at or in the contralateral ovary. For example, if the tumor resides at or in the left ovary, the method comprises distally administering the immunogenic composition to the right ovary. For example, if the tumor resides at or in the right ovary, the method comprises distally administering the immunogenic composition to the left ovary.

D. Pharmaceutical Compositions and Formulations

Also provided are immunogenic compositions comprising an allogeneic leukemia-derived cell of the present disclosure, including pharmaceutical compositions and formulations, such as unit dose form compositions. The pharmaceutical compositions and formulations generally include one or more optional pharmaceutically acceptable carrier or excipient. In certain embodiments, the composition includes at least one additional therapeutic agent (e.g., a second therapy having cytostatic or anticancer activity). Therapies of the present disclosure can be constituted in a composition, e.g., a pharmaceutical composition (e.g., an immunogenic pharmaceutical composition) containing an allogeneic leukemia-derived cell and optionally a pharmaceutically acceptable carrier.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. Accordingly, there are a variety of suitable formulations. A pharmaceutically acceptable carrier includes, but is not limited to, a buffer, excipient, stabilizer, or preservative. In certain embodiments, the choice of carrier is determined in part by the particular cell and/or by the method of administration. A pharmaceutically acceptable carrier includes any and all solvents, dispersion media, coatings, antibacterial and antifungal agents, isotonic and absorption delaying agents, and the like that are physiologically compatible. In certain embodiments, the carrier for a composition containing an allogeneic leukemia-derived cell is suitable for intravenous, intramuscular, subcutaneous, parenteral, spinal or epidermal administration (e.g., by injection or infusion). In certain embodiments, where suitable, e.g., a small molecule based second therapy, the carrier for a composition containing the second therapy is suitable for non-parenteral, e.g., oral administration. A pharmaceutical composition of the disclosure can include one or more pharmaceutically acceptable salts, anti-oxidant, aqueous and non-aqueous carriers, and/or adjuvants such as preservatives, wetting agents, emulsifying agents and dispersing agents. In some embodiments, the pharmaceutical composition can contain preservatives. Suitable preservatives may include, for example, methylparaben, propylparaben, sodium benzoate, and benzalkonium chloride. In certain embodiments, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in certain embodiments are included in the compositions. Suitable buffering agents include, for example, citric acid, sodium citrate, phosphoric acid, potassium phosphate, and various other acids and salts. In certain embodiments, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, e.g., those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In certain embodiments, the cell populations are administered parenterally. The term "parenteral," as used herein, includes intravenous, intramuscular, subcutaneous, rectal, vaginal, and intraperitoneal administration. In certain embodiments, the cells are administered to the subject using peripheral systemic delivery by intravenous, intraperitoneal, or subcutaneous injection.

In certain embodiments, a method for treating a progressive cancer comprises administering an immunogenic composition comprising an allogeneic leukemia-derived cell, wherein the immunogenic composition further comprises a pharmaceutically acceptable carrier. In certain embodiments, the immunogenic composition is formulated for intradermal administration. In certain embodiments, the administration of the immunogenic composition is intradermal. In certain embodiments, the immunogenic composition is formulated for intraperitoneal administration. In certain embodiments, the administration of the immunogenic composition is intraperitoneal. In certain embodiments, the immunogenic composition is formulated for intratumoral administration. In certain embodiments, the administration of the immunogenic composition is intratumoral.

In certain embodiments, the immunogenic composition is formulated for loco-regional lymph node administration. In certain embodiments, the administration of the immunogenic composition is into a loco-regional lymph node. In certain embodiments, loco-regional lymph node administration is performed during or following an initial treatment of the ovarian cancer. In certain embodiments, loco-regional lymph node administration is performed during or following an initial treatment of the ovarian cancer, wherein the initial treatment comprises surgery.

Compositions in certain embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations. The formulations to be used for in vivo administration are generally sterile. Sterility may be readily accomplished, e.g., by filtration through sterile filtration membranes.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present disclosure can be administered via one or more routes of administration using one or more of a variety of methods well known in the art. As will be appreciated by the skilled artisan, the route and/or mode of administration will vary depending upon the desired results.

E. Combination Therapy

Methods provided herein are useful in the treatment of a progressive ovarian cancer by themselves, or in combination with other therapies. As such, also provided herein are combination therapies for use in combination with the methods described herein. For example, methods provided herein can be used in combination with radiation therapy, or with a second therapy having cytostatic or anticancer activity.

In certain embodiments, a method of treating a progressive ovarian cancer as described herein further comprises administering to a subject a second therapy. In some embodiments, the second therapy comprises an effective amount of a second composition. In some embodiments, the second therapy comprises radiation therapy. In some embodiments, the second therapy comprises an immune checkpoint therapy. In some embodiments, the second therapy comprises an anti-angiogenesis therapy. In some embodiments, the second therapy comprises a poly (ADP-ribose) polymerase (PARP) inhibitor therapy. Those of skill in the art (e.g., physicians) would readily be able to determine the specific dosages and dosing regimens useful for a combination therapy described herein.

In certain aspects, methods provided herein are useful in combination with a second therapy having cytostatic or anticancer activity. Suitable cytostatic chemotherapy compounds include, but are not limited to DNA cross-linking agents, DNA-fragmenting agents, intercalating agents, protein synthesis inhibitors, topoisomerase I and II inhibitors, antimetabolites, microtubule-directed agents, kinase inhibitors, hormones and hormone antagonists.

In certain aspects, methods provided herein are useful in combination with a second therapy comprising one or more immuno-oncology (IO) agents. IO agents are known to be effective in enhancing, stimulating, and/or upregulating immune responses in a subject. In certain embodiments, use of an IO agent in combination with a method of treating a progressive ovarian cancer described herein, results in a synergistic effect in treating the progressive ovarian cancer. Examples of IO agents include, without limitation, small molecule drugs, antibodies, and cell-based agents. In certain embodiments, an IO agent is a monoclonal antibody, which can be a human antibody or humanized antibody.

The IO agent can be an agonist of a stimulatory receptor (e.g., a costimulatory receptor), or an antagonist of an inhibitory signal on T cell. The result of both include the amplification of antigen-specific T cell responses. Such IO agents are also referred to in the art as immune checkpoint regulators (e.g., immune checkpoint inhibitors). In some embodiments, IO agents regulate costimulatory and/or coinhibitory pathways, and are capable of augmenting and/or restoring the function of antigen-specific T cell responses. Examples of molecules involved in costimulatory and/or coinhibitory pathways include, without limitation, members of the immunoglobulin superfamily (IgSF); members of the B7 family of membrane proteins, including, for example, B7-1, B7-2, B7-H1 (PD-L1), B7-DC (PD-L2), B7-H2 (ICOS-L), B7-H3, B7-H4, B7-H5 (VISTA), and B7-H6; members of the tumor necrosis factor (TNF) superfamily, including, for example, CD40, CD40L, OX-40, OX-40L, CD70, CD27L, CD30, CD30L, 4-1 BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, and NGFR.

Accordingly, in certain embodiments, the immune checkpoint therapy comprises the use of one or more immune checkpoint regulators that are (i) antagonists of a protein that inhibits T cell activation (e.g., immune checkpoint inhibitors), including, for example, CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; and (ii) agonists of a protein that stimulates T cell activation, including, for example, B7-1, B7-2, CD28, 4-1BB (CD137), 4-1BBL, ICOS, ICOS-L, OX40, OX40L, GITR, GITRL, CD70, CD27, CD40, DR3 and CD28H.

In certain embodiments, the second therapy as described herein may target one or more immune checkpoint regulators. Immune checkpoint regulators that may be targeted by a second therapy (e.g., an immune checkpoint inhibitor) of the present disclosure may include, without limitation, adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3), V-domain Ig suppressor of T cell activation (VISTA), and NKG2A.

In certain embodiments, a method of treating a progressive ovarian cancer as described herein, further comprises administering to the subject an effective amount of an immune checkpoint inhibitor. In certain exemplary embodiments, the immune checkpoint inhibitor targets an immune checkpoint regulator selected from the group consisting of CTLA-4, PD-1, PD-1, NKG2A, B7-H3, and B7-H4. In certain embodiments, immune checkpoint inhibitors may be small molecules, recombinant ligands, recombinant receptors, or antibodies. Immune checkpoint inhibitor antibodies may be humanized, human, chimerized, or any form of antibodies known in the art. Accordingly, in certain exemplary embodiments, the immune checkpoint inhibitor is an antibody selected from the group consisting of anti-CTLA-4, anti-PD-1, anti-PD-L1, anti-CD47 anti-NKG2A, anti-B7-H3, and anti-B7-H4. In certain embodiments, the immune checkpoint inhibitor is an antibody selected from the group consisting of ipilimumab, pembrolizumab, nivolumab, atezolizumab, avelumab, durvalumab, and cemiplimab.

In certain embodiments, the immune checkpoint inhibitor is a PD-1 binding antagonist, a molecule that is capable of inhibiting the binding of PD-1 to its ligand binding partners. In certain embodiments, the PD-1 ligand binding partners are PD-L1 and/or PD-L2. In some embodiments, a PD-L1 binding antagonist is a molecule that inhibits the binding of PDL1 to its binding partners. In some embodiments, PD-L1 binding partners are PD-1 and/or B7-1. In some embodiments, the PD-L2 binding antagonist is a molecule that inhibits the binding of PD-L2 to its binding partners. In some embodiments, a binding partner of PD-L2 is PD-1. Exemplary antibodies are described in U.S. Pat. Nos. 8,735,553, 8,354,509, and 8,008,449, the disclosure of which are incorporated herein by reference in their entireties.

In some embodiments, the immune checkpoint inhibitor is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. Nivolumab, also known as MDX-1106-04, MDX-1106, ONO-4538, BMS-936558, and OPDIVO, is an anti-PD-1 antibody described in International Patent Application No. WO2006/121168, the disclosure of which is incorporated herein in its entirety. Pembrolizumab, also known as MK-3475, Merck 3475, lambrolizumab, KEYTRUDA, and SCH-900475, is an anti-PD-1 antibody described in International Patent Application No. WO2009/114335, the disclosure of which is incorporated herein in its entirety. CT-011, also known as Pidilizumab, is an anti-PD-1 antibody described in International Patent Application No. WO2009/101611, the disclosure of which is incorporated herein in its entirety. Additional anti-PD-1 antibodies include PDR001 (Novartis; see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHR1210 (SHR-1210) (Incyte/Jiangsu Hengrui Medicine; see WO2015/085847), TSR-042 (ANB001) (Tesara/AnaptysBio; see WO2014/179664), GLS-010 (Wuxi/Harbin Gloria Pharmaceuticals), AM-0001 (Armo/Ligand), or STI-1110 (Sorrento; see WO2014/194302).

In certain embodiments, the immune checkpoint inhibitor is a PD-L1 binding antagonist, such as an antagonistic PD-L1 antibody. Exemplary anti-PD-L1 antibody can be selected from Tecentriq (atezolizumab), durvalumab, avelumab, cemiplimab, STI-1014 (Sorrento; see WO2013/181634), or CX-072 (CytomX; see WO2016/149201). In some embodiments, the immune checkpoint inhibitor is a PD-L1 antagonist such as Durvalumab, also known as MED14736, atezolizumab, also known as MPDL3280A, or avelumab, also known as MSB00010118C.

In certain embodiments, the immune checkpoint inhibitor is a CTLA-4 binding antagonist, a molecule that is capable of inhibiting the binding of CTLA-4 to its ligand binding partners. CTLA-4 is found on the surface of T cells and acts as an "off" switch when bound to CD80 or CD86, also called B7-1 and B7-2 respectively, on the surface of antigen-presenting cells. CTLA4 is a member of the immunoglobulin superfamily that is expressed on the surface of Helper T cells and transmits an inhibitory signal to T cells. In some embodiments, the immune checkpoint inhibitor is an anti-CTLA-4 antibody (e.g., a human antibody, a humanized antibody, or a chimeric antibody). Anti-CTLA-4 antibodies are disclosed in U.S. Pat. No. 8,119,129, International Patent Application Nos. WO 01/14424, WO 98/42752; WO 00/37504 (CP675,206, also known as tremelimumab; formerly ticilimumab), U.S. Pat. No. 6,207,156; Hurwitz et al., 1998, the disclosures of which are incorporated herein by reference in their entireties. Antibodies that compete with any of these art-recognized antibodies for binding to CTLA-4 also can be used, for example, a humanized CTLA-4 antibody is described in International Patent Application Nos. WO2001014424, WO2000037504, and U.S. Pat. No. 8,017,114, the disclosures of which are incorporated herein by reference in their entireties. Exemplary anti-CTLA-4 antibodies include, ipilimumab (also known as 10D1, MDX-010, MDX-101, and YERVOY®).

In certain embodiments, the immune checkpoint inhibitor is an antibody to B7-H4 (e.g., those disclosed in International Patent Application Nos. WO 2013025779 and WO2013067492, the disclosures of which are incorporated by reference herein in their entireties). In certain embodiments, the immune checkpoint inhibitor is an antibody to B7-H3, including without limitation antibodies neutralizing human B7-H3 (e.g. MGA271 disclosed as BRCA84D and derivatives in U.S. Patent Publication No. 20120294796, the disclosure of which is incorporated by reference herein in its entirety). In certain embodiments, the immune checkpoint inhibitor is an antibody to NKG2A, see, e.g., Montfoort et al. *Cell* (2018) 175(7):1744-1755, the disclosure of which is incorporated by reference herein in its entirety.

In certain embodiments, the immune checkpoint inhibitor is a macrophage checkpoint blockade. For example, CD47 has been identified as a dominant macrophage checkpoint, and is found to be overexpressed in myeloid malignancies that leads to tumor evasion of phagocytosis by macrophages. CD47 blockade has been shown to result in the engulfment of leukemic cells, and pre-clinical data has shown anti-cancer activity in multiple hematologic malignancies including AML and myelodysplastic syndrome (MDS). See, e.g., Chao et al. *Frontiers in Oncology* (2019) 9:1380. Accordingly, in certain embodiments, the immune checkpoint inhibitor is an antibody to CD47.

In certain aspects, methods provided herein are useful in combination with a second therapy comprising one or more anti-angiogenic agents. Accordingly, methods provided herein are useful in combination with anti-angiogenesis therapy. The formation of new blood vessels, or angiogenesis, facilitates cancer growth and metastasis by providing a tumor with dedicated blood supply to provide oxygen and essential nutrients required for its growth. Therapies targeting angiogenesis and associated growth factors including, without limitation, vascular endothelial growth factor (VEGF), platelet-derived growth factor (PDGF), and fibroblast growth factor (FGF), have been shown to inhibit new blood vessel growth.

Many anti-angiogenic agents are known in the art and would be suitable for use in combination with a method provided herein. Exemplary anti-angiogenic agents include, without limitation, physiological agents such as growth factors (e.g., ANG-2, NK1, 2, 4 (HGF), transforming growth factor beta (TGF-β)), cytokines (e.g., interferons such as IFN-α, -β, -γ, platelet factor 4 (PF-4), PR-39), proteases (e.g., cleaved AT-III, collagen XVIII fragment (Endostatin)), HmwKallikrein-d5 plasmin fragment (Angiostatin), prothrombin-F1-2, TSP-1), protease inhibitors (e.g., tissue inhibitor of metalloproteases such as TIMP-1, -2, or -3; maspin; plasminogen activator-inhibitors such as PAI-1; pigment epithelium derived factor (PEDF)), Tumstatin, antibody products (e.g., the collagen-binding antibodies HUIV26, HU177, XL313; anti-VEGF: anti-integrin (e.g., Vitaxin, (Lxsys))), and glycosidases (e.g., heparinase-I or -II). Also suitable are molecules that are antagonists to angiogenesis-associated antigens (including proteins and polypeptides), including, without limitation, molecules directed against VEGF, VEGF receptor, EGFR, bFGF, PDGF-B, PD-ECGF, TGFs including TGF-α, endoglin, Id proteins, various proteases, nitric oxide synthase, aminopeptidase, thrombospondins, k-ras, Wnt, cyclin-dependent kinases, microtubules, heat shock proteins, heparin-binding factors, synthases, collagen receptors, integrins, and surface proteoglycan NG2. "Chemical" or modified physiological agents known or believed to have anti-angiogenic potential include, for example, vinblastine, TAXOL®, ketoconazole, thalidomide, dolestatin, combrestatin A, rapamycin (Guba, et al. *Nature Medicine* (2002) 8:128-135, the disclosure of which is incorporated by reference herein in its entirety), CEP-7055 (available from Cephalon, Inc.), flavone acetic acid, Bay 12-9566 (Bayer Corp.), AG3340 (Agouron, Inc.). CGS. 27023A (Novartis), tetracylcine derivatives (e.g., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protarnine), cationic peptide-VEGF, Suramin (polysulphonated napthyl urea), compounds that interfere with the function or production of VEGF (e.g., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (e.g., squalamine), glutathione analogues (e.g., N-acteyl-L-cysteine), combretastatin A-4 (Oxigene), Eph receptor blocking agents (Himanen et al. *Nature* (2001) 414 (6866): 933-938, the disclosure of which is incorporated by reference herein in its entirety), Rh-Angiostatin, Rh-Endostatin (see, International Patent Application No. WO 01/93897, the disclosure of which is incorporated by reference herein in its entirety), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phenyl-alanine-N-methylamides (e.g., Batimistat, Marimastat), AG3340, and minocycline.

In certain embodiments, the anti-angiogenesis agent is an anti-VEGF antibody. Exemplary anti-VEGF antibodies include any antibodies, or antigen binding fragments thereof, that bind with sufficient affinity and specificity to VEGF and can reduce or inhibit the biological activity of VEGF. In certain embodiments, anti-VEGF antibodies include, without limitation, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. *Cancer Research* (1997) 57:4593-4599, the disclosure of which is incorporated by reference herein in its entirety. In certain embodiments, the anti-VEGF antibody is Bevacizumab (BV), also known as rhuMAb VEGF or AVASTIN. Bevacizumab and other humanized anti-VEGF antibodies are further described in U.S. Pat. No. 6,884,879, the disclosure of which is incorporated by reference herein in its entirety. Additional antibodies include, e.g., G6-31 and B20-4.1, as described in International Patent Application Nos. WO2005/012359 and WO2005/044853, the disclosures of which are incorporated by reference herein in their entireties. Additional anti-VEGF antibodies are described in the following U.S. Pat. Nos. 7,060,269, 6,582,959, 6,703,020, and 6,054,297; International Patent Publication Nos. WO98/45332, WO 96/30046, and WO94/10202; European Patent No. EP 0666868B1; U.S. Patent Publication Nos. 2006009360, 20050186208, 20030206899, 20030190317, 20030203409, and 20050112126; and Popkov et al., Journal of Immunological Methods 288:149-164 (2004), the disclosures of which are incorporated by reference herein in their entireties. Additional VEGF inhibitors include Sunitinib (SUTENT®, Pfizer) and sorafenib (NEXAVAR®, Onyx and Bayer Healthcare Pharmaceuticals) which belong to a group of VEGF-receptor tyrosine-kinase inhibitors (RTKIs) with activity against both VEGFR and PDGFR. In certain embodiments, the anti-angiogenesis agent is sunitinib. Yet other VEGF inhibitors include fusion proteins that prevent ligand binding to vascular endothelial growth factor receptors (VEGFR). These fusion proteins are sometimes referred to as VEGF traps, and include aflibercept. Accordingly, in certain embodiments, the anti-angiogenesis therapy comprises an anti-angiogenesis agent selected from the group consisting of bevacizumab, aflibercept, sunitinib, and sorafenib.

In certain aspects, methods provided herein are useful in combination with a second therapy comprising one or more poly (ADP-ribose) polymerase (PARP) inhibitors. Accordingly, methods provided herein are useful in combination with PARP inhibitor therapy. PARP is a family of proteins involved in many functions in a cell, including DNA repair, gene expression, cell cycle control, intracellular trafficking and energy metabolism. PARP proteins play key roles in single strand break repair through the base excision repair pathway. PARP inhibitors have shown activity as a monotherapy against tumors with existing DNA repair defects, such as BRCA1 and BRCA2, and as a combination therapy when administered together with anti-cancer agents that induce DNA damage. The PARP inhibitor may be selected from the group consisting of a small molecule, a nucleic acid, a nucleic acid analog or derivative, a peptide, a peptidomimetic, a protein, an antibody or an antigen-binding fragment thereof, a monosaccharide, a disaccharide, a trisaccharide, an oligosaccharide, a polysaccharide, a lipid, a glycosaminoglycan, an extract made from a biological material, and combinations thereof. Exemplary PARP inhibitors include, without limitation, olaparib, veliparib or a prodrug thereof, rucaparib, talazoparib, niraparib, INO-1001, AZD2461, SC10914, BGB-290, and Fluzoparib. Accordingly, in certain embodiments, the PARP inhibitor therapy comprises a PARP inhibitor selected from the group consisting of olaparib, niraparib, rucaparib, and veliparib.

Combination therapies described herein comprising a method useful in the treatment of a progressive ovarian cancer (e.g., a progressive ovarian cancer therapy described herein) and a second therapy (e.g., immune checkpoint therapy, anti-angiogenesis therapy, PARP inhibitor therapy) encompass treatment regimens wherein the progressive ovarian cancer therapy and the second therapy are simultaneously (e.g., substantially simultaneously) or sequentially administered to a subject. For example, a progressive ovarian cancer therapy described herein can be substantially simultaneously administered to a subject together with the second therapy. Substantially simultaneous administration can be accomplished, for example, by administering to the subject a single dosage form having a fixed ratio of each therapy or in multiple, single dosage forms for each therapy. Each therapy can be sequentially or substantially simultaneously administered by any appropriate route including, without limitation, oral routes, intravenous routes, intratumoral routes, intramuscular routes, and direct absorption through mucous membrane tissues.

In some embodiments, the progressive ovarian cancer therapy and the second therapy are administered by the same route or by different routes. For example, a progressive ovarian cancer therapy of the combination selected may be administered by intravenous injection while the second therapy of the combination may be administered intratumorally. Alternatively, for example, all therapies may be administered intravenously or all therapeutic agents may be administered by intratumorally.

In some embodiments, a combination therapy can include the administration of the progressive ovarian cancer therapy and the second therapy, in combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapies and non-drug treatment is achieved.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present disclosure has been described with reference to the specific embodiments thereof, it should be understood by those skilled in the art that various changes may be made and equivalents may be substituted without departing from the true spirit and scope of the disclosure. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present disclosure. All such modifications are intended to be within the scope of the claims appended hereto. Having now described certain embodiments in detail, the same will be more clearly understood by reference to the following examples, which are included for purposes of illustration only and are not intended to be limiting.

F. Experimental Examples

Figure 1B:
Figure 1B:
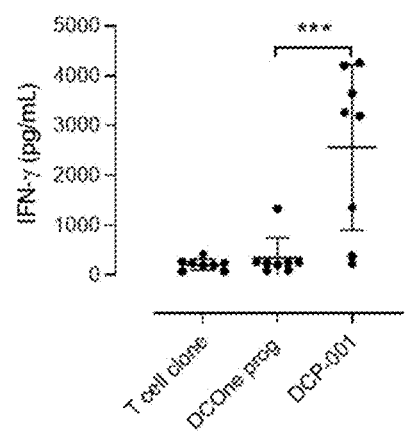
Figure 1C:
Figure 1C:
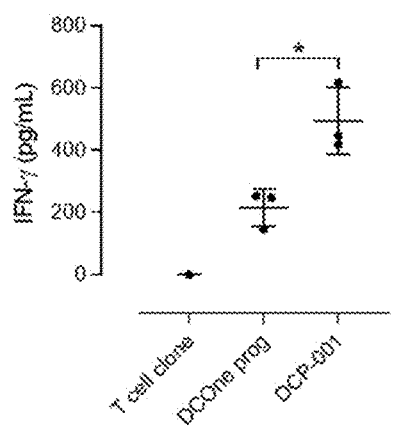
Figure 1D:
Figure 1D:
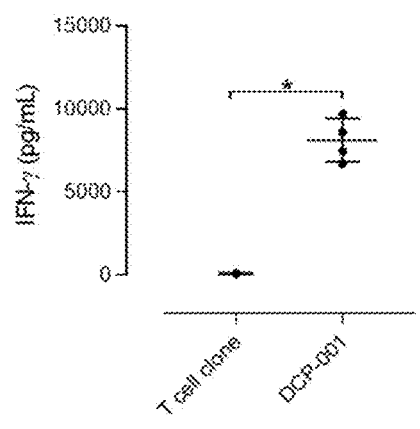

Example 1: DCP-001 (DCOne Derived mDCs) can Stimulate T-Cells Directed Against Both Endogenous and Exogenous Antigens Ex Vivo DCOne mDCs were found to stimulate antigen-specific T-cell clones directed against endogenous antigens expressed by the DCOne cell line (FIG. 1A-FIG. 1D). FIG. 1A shows the response of PRAME T cell clones to DCP-001; FIG. 1B shows the response of WT-1 T cell clones to DCP-001; FIG. 1C shows the response of MUC-1 T cell clones to DCP-001; and FIG. 1D shows the response of RHAMM T cell clones to DCP-001.

In FIG. 1A, irradiated DCOne progenitors or DCP-001 were incubated with three PRAME-specific T-cell clones and one CMV pp65-specific T cell clone, at a stimulator: responder ratio of 5:1 in round-bottom 96-wells culture plates for 18 hours. IFN-γ production was analyzed in culture supernatants employing ELISA. T-cell clones only, without DCOne-derived cells, served as negative control. Data shown are from three different DCOne-derived cell batches, each performed in duplicate. IFN-γ levels (pg/mL) are presented as mean±SD. One-way ANOVA multiple comparison was used to calculate p-values. *=p<0.05

In FIG. 1B, irradiated DCOne progenitor or DCP-001 cells were incubated with HLA-A2 restricted CD8+ T-cell clone specific for WT[126-134], at a stimulator: responder ratio of 1:5 in round-bottom 96-wells culture plates for 24 hours. IFN-γ production was analyzed in culture supernatants employing ELISA. T-cell clone only, without DCOne-derived cells, served as negative control. Horizontal lines indicate mean±SD from n=8 experiments. One-way ANOVA multiple comparison was used to calculate p-values. ***=p<0.0005.

In FIG. 1C, irradiated DCOne progenitor or DCP-001 cells were incubated with a HLA-A2 restricted CD8+ T-cell clone specific for MUC-1[950-958], at a stimulator: responder ratio of 1:5 in round-bottom 96-wells culture plates for 24 hrs. IFN-γ production was analyzed in culture supernatants employing ELISA. T-cell clone only, without DCP-001, served as negative control.

Data shown are from 4 different DCP-001 batches, each performed in triplicates. One-way ANOVA multiple comparison was used to calculate p-values. *=p<0.05 In FIG. 1D, irradiated DCP-001 cells were incubated with HLA-A2 restricted CD8+ T-cell clone specific for RHAMM[165-173], at a stimulator: responder ratio of 1:5 in round-bottom 96-wells culture plates for 24 hours. IFN-γ production was analyzed in culture supernatants employing ELISA. T-cell clone only, without DCP-001, served as negative control. Data shown are from 3 different DCP-001 batches, each performed in triplicates. One-way ANOVA multiple comparison was used to calculate p-values. *=p<0.05.

Figure 2:
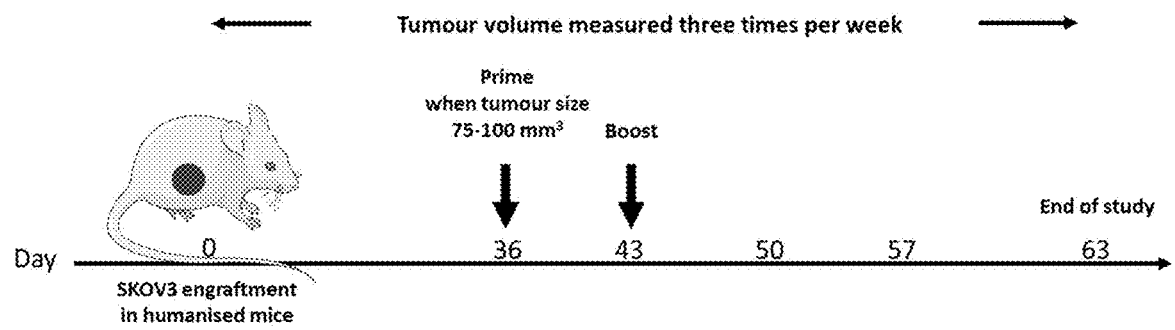
FIG. 2 depicts a schematic showing a vaccination strategy of an SKOV3 engrafted ovarian cancer mouse model, according to one embodiment.

Example 2: Efficacy of DCP-001 in a Humanized Ovarian Cancer Mouse Model: Vaccination Away from Tumor Site FIG. 2 depicts a schematic showing a vaccination strategy of an SKOV3 engrafted ovarian cancer mouse model. SKOV3 tumours were engrafted in humanized mice. DCP-001 was administered via intraperitoneal (IP) vaccination of 0.2E6 cells/mouse in prime boost fashion. Prime vaccination occurred on 36 days post-engraftment when tumor size was measured to be 75-100 mm$^3$. Boost vaccination occurred on 43 days post-engraftment. Controls were vaccinated with phosphate buffered saline (PBS) on days 36 and 43 post-engraftment. Tumor volume was measured three times a week until 63 days post-engraftment.

Figure 3:
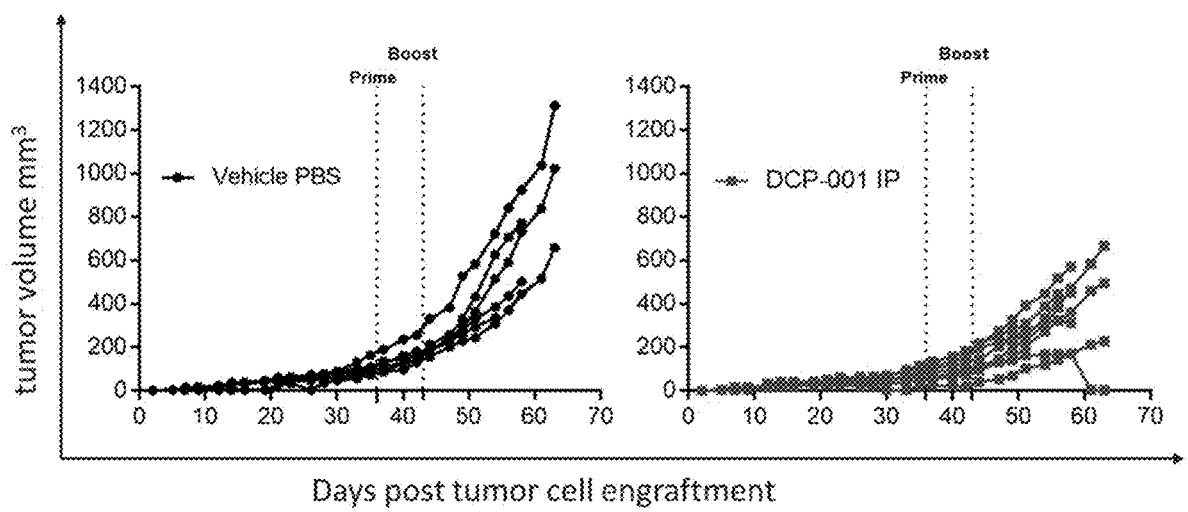
FIG. 3 depicts graphs showing the tumor volume (in mm$^3$) measured over time in SKOV3 tumor engrafted mice administered a vaccination strategy according to FIG. 2.

FIG. 3 depicts graphs showing the tumor volume (in mm$^3$) measured over time in SKOV3 tumor engrafted mice administered a vaccination according to FIG. 2. As shown in FIG. 3, tumor growth in DCP-001 vaccinated mice was found to be reduced compared to the control group (vaccinated with PBS). In one mouse in the DCP-001 vaccinated group, tumor regression was observed.

Example 3: Efficacy of DCP-001 in a Humanized Ovarian Cancer Mouse Model: Different Vaccination Strategies FIG. 4 depicts a schematic showing a vaccination strategy of an SKOV3 engrafted ovarian cancer mouse model. SKOV3 tumors were engrafted in humanized mice. DCP-001 relapse vaccination was tested (n=9). Relapse vaccination aimed to prevent tumour recurrence following initial treatment. In the experimental setting, it is mimicked by vaccinating animals prior to tumor engraftment. In the relapse vaccination schedule: DCP-001 relapse vaccination of 0.2E6 cells/mouse were administered IP on days −13 and −6. Controls were vaccinated with PBS on days −13, −6, 13, and 43 (n=8).

Figure 5C:
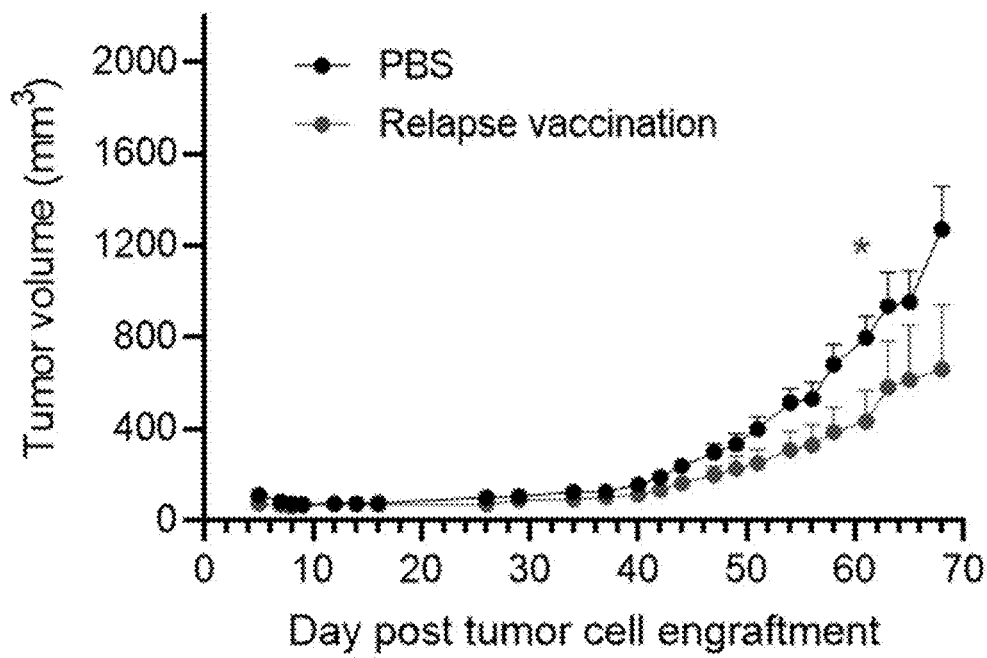

FIG. 5A and FIG. 5B depict graphs showing the tumor volume (in mm$^3$) measured over time in SKOV3 tumor engrafted mice administered control vaccination (PBS; FIG. 5A); or relapse vaccination (FIG. 5B). As shown in FIG. 5A and FIG. 5B, tumor growth in DCP-001 relapse vaccinated mice was reduced compared to the control group. In addition, tumor regression was observed in five mice (three total and two partial regressions) of the relapse vaccinated group. FIG. 5C depicts a graph showing the mean tumor volume (in mm$^3$) per group measured over time in SKOV3 tumor engrafted mice administered control vaccination (PBS) or relapse vaccination. In FIG. 5C, from day 56 onwards the number of animals per group decreased as they needed to be sacrificed based on their health status, resulting in 6 animals per group at the end of the study. * indicates p<0.05, unpaired t-test at day 61.

Figure 5D:
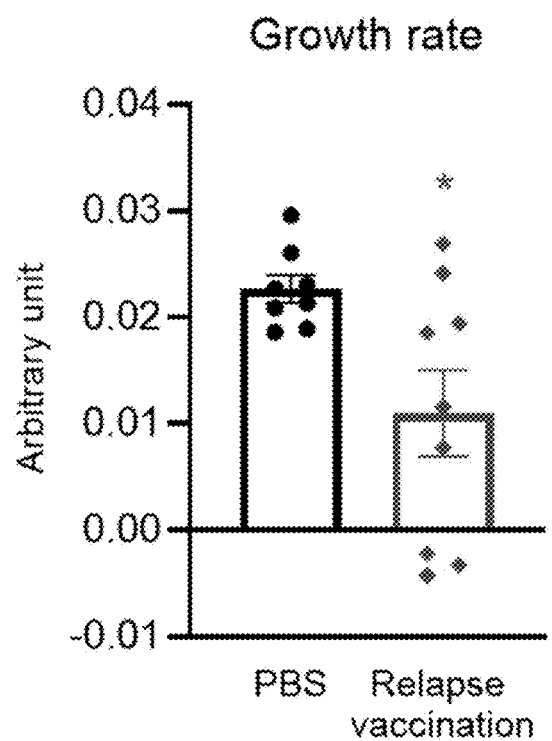

FIG. 5D depicts a graph showing the average tumor growth rate from 5 days after tumor engraftment until end of the study, determined by method of Hather et al. *Cancer Inform.* (2014) 13(Suppl 4):65-72, the disclosure of which is incorporated by reference herein in its entirety. Symbols and bars (±SEM) represent average tumor growth rates of each individual animal and per treatment group. * indicates p<0.05, unpaired t-test. As shown in FIG. 5D, the tumor growth rate was decreased in animals administered the relapse vaccination as compared to animals that were administered PBS as controls.

Figure 6A:
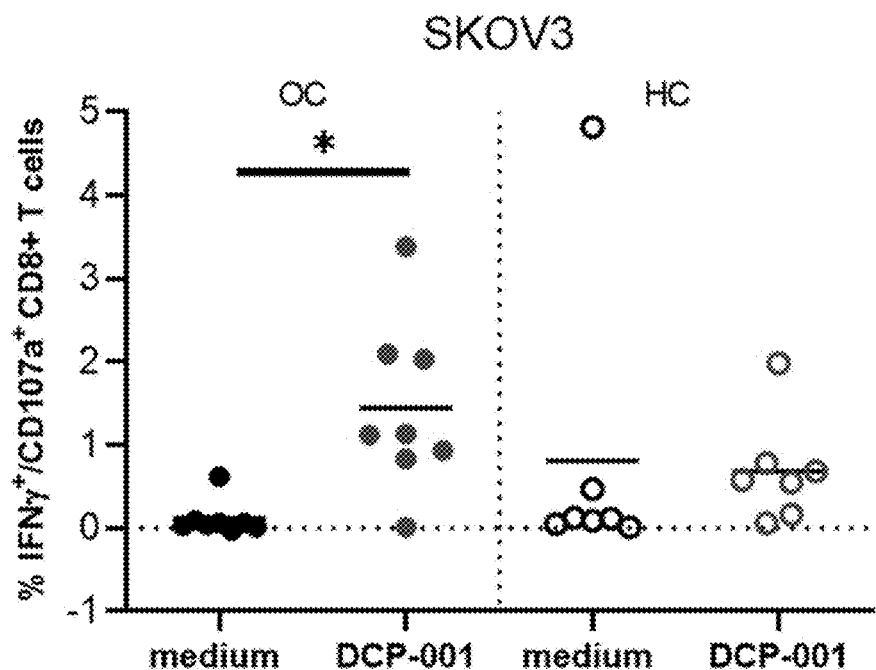
FIG. 6A-FIG. 6B depict graphs showing that DCOne mDCs induce cytotoxic T cell responses towards the SKOV3 and OV90 ovarian cancer cell lines, respectively.
Figure 6B:
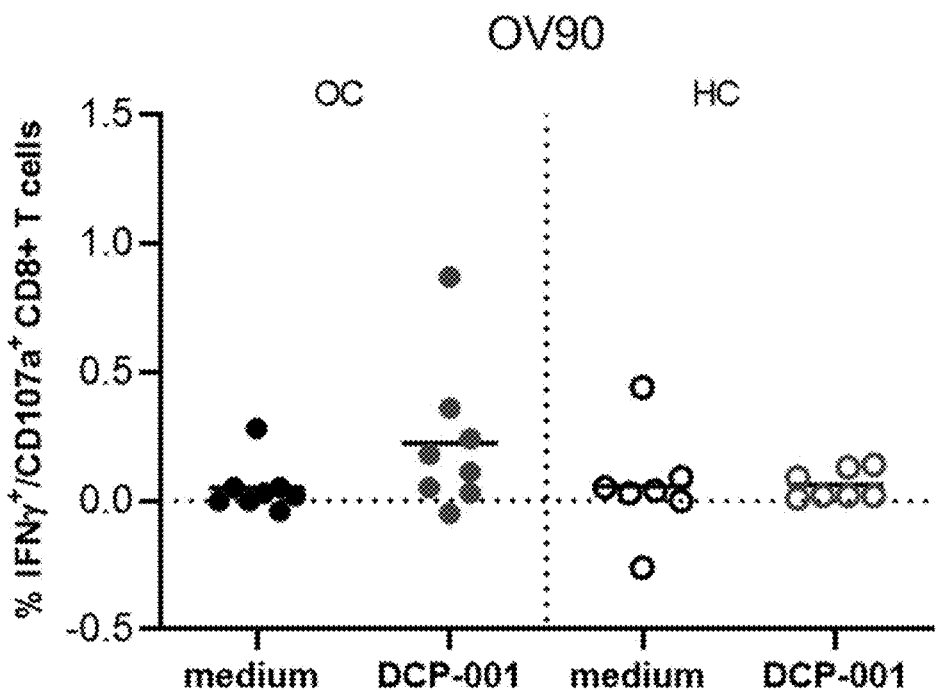

Example 4: DCP-001 Stimulates Cytotoxic T Cell Responses Towards Ovarian Cancer Cells in PBMC of Ovarian Cancer Patients FIG. 6A and FIG. 6B depict graphs showing that DCOne mDCs induced cytotoxic T cell responses towards the SKOV3 and OV90 ovarian cancer cells, respectively. The cytotoxic capacity of DCP-001-activated PBMC was determined in co-cultures with ovarian cancer target cells SKOV3 and OV90. PBMCs from ovarian cancer patients (OC; n=8) or heathy controls (HC; n=7) were co-cultured with medium or DCP-001 for 21 days. Cytotoxicity was measured by incubation of the medium- or DCP-001-stimulated PBMCs (effector cells) for approximately 6 hours with cells from ovarian cancer cell lines SKOV3 (FIG. 6A) or OV90 (FIG. 6B) (target cells) at a Target: Effector ratio of 1:10 in the presence of anti-CD107a antibody (marker for cytotoxicity). Hereafter cells were stained for T cell surface markers followed by an intracellular IFN-γ staining, and measured by flow cytometry. Data from 5 independent experiments are shown; each dot represents the mean of results obtained using PBMC from one individual donor; the horizontal bar represents the mean of all donors. In FIG. 6A, * indicates p<0.05 by repeated measures 1-way ANOVA.

Figures 6C, 6D:
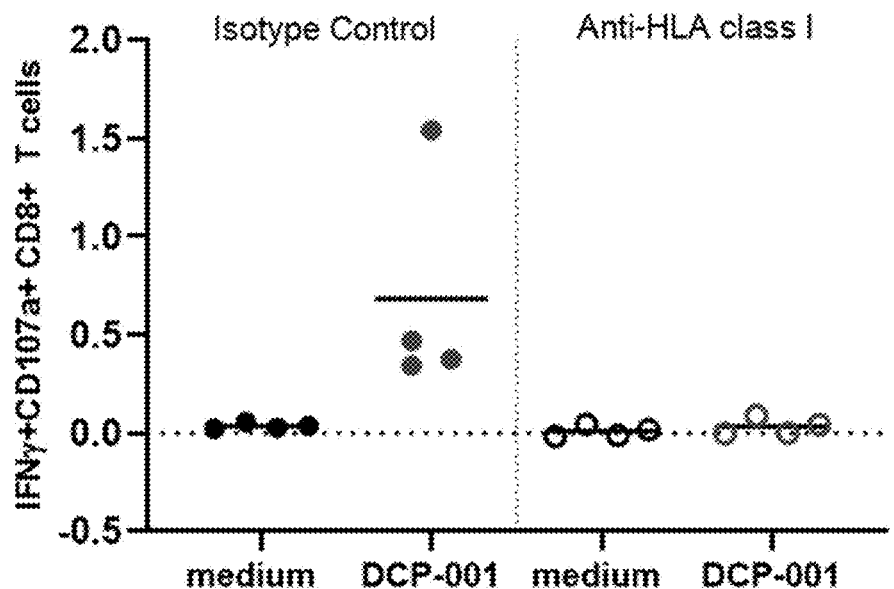
FIG. 6C depicts a graph showing DCOne mDC induced cytotoxic T cell responses towards the SKOV3 ovarian cancer cell line in the presence of an anti-HLA class I antibody or an isotype control.
FIG. 6D is a table showing the number of individuals over the total number of individuals from whom PBMC after a 21-day co-culture with DCP-001 versus medium alone showed increased percentages of IFNγ+CD107a+CD8+ T cells towards ovarian cancer cell lines SKOV3 or OV90.

The same procedure was repeated in the presence of either anti-HLA class I antibody or isotype control during the cytotoxicity test with SKOV3 for PBMC from four ovarian cancer patients (FIG. 6C). As shown in FIG. 6C, the cytotoxicity of DCP-001-activated PBMC obtained from ovarian cancer patients was diminished in the presence of an anti-HLA class I antibody.

FIG. 6D is a table showing the number of individuals/total number of individuals from whom PBMC after a 21-day co-culture with DCP-001 versus medium alone showed increased percentages of IFNγ+CD107a+CD8+ T cells towards ovarian cancer cell lines SKOV3 or OV90. [1]+++ indicates ≥10-fold increase; ++ indicates 5- to 10-fold increase; + indicates 3- to 5-fold increase, or when the medium alone culture yielded percentages s 0 with DCP-001 co-culture percentage >0. One OC patient showed a negative response score, due to a pre-existing response to both SKOV3 and OV90 which was not further enhanced by ex-vivo stimulation with DCP-001. OC represents ovarian cancer.

The above examples show that DCP-001 vaccination reduced ovarian cancer tumor growth in a humanized mouse model. Without being bound to any theory, DCP-001 was shown to result in the activation of cellular immunity against ovarian cancer cells in PBMC of ovarian cancer patients in vitro. The data confirm that DCOne cells can be used as a basis for vaccines against ovarian cancer.

Example 5: DCP-001 as Relapse Vaccine in Patients with Ovarian Cancer Rationale Ovarian cancer (OC) is the leading cause of death from gynecological malignancies with a 5-year survival of no more than 40%. Current standard treatment (surgery and chemotherapy) is initially effective, but almost all patients suffer from chemotherapy-resistant relapse. After cytoreductive surgery (complete/suboptimal), most patients remain in a state of microscopic minimal residual disease until relapse. Therefore, new approaches that improve therapeutic outcome for OC patients are urgently needed. In this example, a novel immunotherapy is proposed using an allogeneic cell-based vaccine (DCP-001), consisting of cells with tumor-associated antigens and characteristics of dendritic cells (DC), as a novel maintenance therapy in OC. Dendritic cells are professional antigen-presenting cells (APCs) and exquisitely suited to induce anti-cancer immune responses.

It is hypothesized that administration of a vaccine after initial treatment has the advantage of eradicating residual tumor cells instead of targeting cancer cells within a fully formed suppressive environment, providing optimal conditions for the immune system to prevent clinical relapse. For this example, the use of maintenance therapy with the allogeneic cell-based vaccine, DCP-001, is proposed.

DCP-001 was developed from an acute myeloid leukemia (AML)-derived cell line that uniquely combines the positive features of allogeneic DC vaccines and expression of multiple tumor associated antigens. Vaccination with DCP-001 in 12 post-remission AML patients prolonged minimal residual disease status and was associated with improved progression free survival (PFS) and systemic immunogenicity. Administration of the vaccine was associated with only limited side-effects like fever, injection site reactions, adenopathy, and fatigue. A phase II trial in AML is currently ongoing. See, van de Loosdrecht et al. *Cancer Immunol. Immunother.* (2018) 67(10):1505-1518, the disclosure of which is incorporated by reference herein in its entirety.

The tumor associated antigens (TAA's) expressed by DCP-001 were found to be shared across different tumor types, most notably also ovarian cancer. These antigens include, but are not limited to, some of the hallmark OC antigens: WT-1, MUC-1, survivin and PRAME. Pre-clinical studies in an ovarian cancer mouse model, as described in Examples 2 and 3, showed efficacy of DCP-001 in reducing tumor growth. Additionally, pre-clinical studies of DCP-001 in peripheral blood cells of OC patients, as described in Example 4, resulted in potent vaccine-induced T cell responses in general and specifically against OC cell lines.

Objectives:
Primary Objective:
- Systemic immunogenicity of the DCP-001 vaccination in high grade serous ovarian (HGSOC) cancer patients.

Secondary Objectives:
- Safety and tolerability of the DCP-001 vaccine.
- Recurrence free survival (RFS) measured by time in months that the patient survives without any signs or symptoms of cancer of primary HGSOC patients treated with the DCP-001 vaccine.
- Overall survival (OS) measured by time in months to death from diagnosis of primary HGSOC patients treated with the DCP-001 vaccine Exploratory Objectives:
- Circulating plasma biomarkers CA125 and circulating tumor DNA will be monitored during study follow up after DCP-001 vaccination.
- Diagnostic imaging (computed tomography, CT) will be performed and analyzed for diagnosing HGSOC recurrence after DCP-001 vaccination.
- Analysis of phenotype, specificity and quantity of peripheral vaccine induced T cells in relationship to pre-treatment intratumoral T cells.
- Characterization of the global peripheral immune profile of HGSOC patients prior to DCP-001 vaccination and changes to this profile thereafter.
- Identify specific T-cell subsets induced or expanded through DCP-001 vaccination and evaluate their capacity to respond to the primary OC diagnosed.

Phase I ALISON Study Design:

The standard of care (SoC) treatment for advanced HGSOC consists of primary debulking surgery (PDS) combined with 6 cycles of adjuvant chemotherapy (ACT) or 3 cycles of neoadjuvant chemotherapy (NACT), interval debulking surgery (IDS) and 3 more cycles of adjuvant chemotherapy. In this example, DCP-001 vaccinations are scheduled after SoC treatment.

Six doses (4 vaccinations and 2 boosters) of DCP-001 vaccine are administered to induce an anti-tumor immune response starting 4 weeks after the last cycle of carboplatin/paclitaxel. Systemic immune responses are determined using peripheral blood mononuclear cells (PBMCs) collected before, during and after vaccinations. Progression of disease is monitored according to standard-of-care follow-up.

Intervention:

Vaccination:

Patients receive 4 intradermal (i.d.) vaccinations (0.5 mL, 25 million cells per vaccination) once every 2 weeks, starting 4 weeks after the last cycle of adjuvant chemotherapy and followed by 2 booster (10 million cells per vaccination) vaccinations in a monthly interval. Patient evaluation is performed before, during and after vaccination, including history, physical examination and toxicity scoring using common toxicity criteria grades (National Cancer Institute Common Terminology Criteria for Adverse Events (NCI CTCAE) Version 5.0). Blood sample collection for bio-monitoring by means of a vena puncture is performed at baseline, prior and after the first four vaccinations and before and after the booster vaccinations (leukapheresis).

Blood Collection for the Primary Endpoint:

200 mL of venous blood is collected at baseline and a leukapheresis (200 mL) will be performed 28 days after final $6^{th}$ vaccination (booster) to determine the primary endpoint. In addition, during the vaccination period, PBMCs (100 mL) is collected at 4 selected time points to assess the induction of the systemic immune response.

Secondary Endpoint:

Standard of care follow-up until relapse, duration of study follow up is 2 years from enrollment for each patient.

Blood Collection for Exploratory Endpoints:

Classical tumor marker CA125 data id collected every 3-4 months. Also, circulating tumor DNA (ctDNA) is simultaneously collected. ctDNA is present in the blood of approximately 56% of all late-stage OC patients and has been suggested as a more sensitive marker for predicting patient relapse. In addition, the presence of DCP-001 tumor associated antigens in ctDNA is determined. In total, 14 mL of peripheral blood (CA125 (4 mL), ctDNA (10 mL)), is collected every 3-4 months after vaccination.

Imaging Collection for Exploratory Endpoint:

A CT scan is performed at baseline and 2 years after vaccination. During follow up, as a part of standard care, imaging may be performed in case the patient is suspect for relapse judged by their treating (gynecologic) oncologist (e.g. ovarian cancer related complaints and/or rising CA125 levels).

Tumor Tissue and PBMCs for Exploratory Endpoint:

Tumor material to analyze vaccine-induced expansion of T cell specificities and the global immune profile present in the tumor prior to vaccination is routinely collected under an existing biobanking protocol during standard-of-care interval surgery (SoC). When patients are included (after surgery and completing adjuvant chemotherapy), tumor tissue is requested from the existing biobank. To analyze the global immune profile of HGSOC prior to the DCP-001 vaccination, PBMCs collected at baseline are analyzed using flow cytometry.

Main Study Endpoint:

To assess the primary endpoint for the trial:
  Systemic DCP-001 antigen specific response is measured by the number of patients with de novo or increased immune responses based on IFN-γ ELISpot assay in the post-vaccination PBMC sample to the DCP-001 vaccination and/or to at least one of the following DCP-001 vaccine antigens compared to baseline: WT-1, MUC-1 or PRAME.

To assess the secondary endpoints for the trial:
  The number of adverse events (AEs), and severe adverse events (SAEs) are analyzed (up to 3 days after the leukapheresis).
  RFS defined as the number of patients alive without any recurrence (local or regional, or distant) and death due to any cause at 2 years from disease diagnosis, is monitored.
  Recurrence (local or regional, or distant) of disease is monitored according to standard-of-care follow-up.
  Overall survival (OS) is measured by time in months to death from diagnosis due to any cause at 2 years from disease diagnosis.

To assess the exploratory endpoints:
  ctDNA, CA125 levels and CT-scans are analyzed.
  Tumor site derived cells are profiled for different immune cell populations by flow cytometry and immunohistochemistry. RNA and single intratumoral T cells are isolated and analyzed (T cell receptor sequencing).
  PBMCs are profiled for different immune cell populations by flow cytometry and T-cell receptor (TCR) sequencing.
  Cytotoxic T-cells directed against patients' tumor tissue after DCP-001 vaccination are analyzed.
  T-cell responses toward antigens not present in DCP-001, such as NY-ESO and MAGE-A3, are analyzed.

What is claimed is:

1. A method of preventing or delaying recurrence of ovarian cancer in a subject comprising:
  selecting a subject previously diagnosed with ovarian cancer, wherein the subject is in remission following an initial treatment for the ovarian cancer selected from the group consisting of debulking surgery, chemotherapy, and radiation therapy; and
  administering to the subject an effective amount of an immunogenic composition comprising a mature dendritic cell differentiated from the precursor DCOne cell line as deposited under the conditions of the Budapest treaty with the DSMZ under accession number DSMZ ACC3189, wherein the mature dendritic cell is CD34-positive, CD1a-positive, and CD83-positive and is inactivated,
  thereby preventing or delaying recurrence of ovarian cancer in the subject.

2. The method of claim 1, wherein:
  the immunogenic composition is formulated for intradermal administration; and
  the administration is intradermal.

3. The method of claim 1, wherein the administering is performed within about two weeks to about six months after the initial treatment for the ovarian cancer.

4. The method of claim 1, wherein the administering is performed within about two weeks to about one month after the initial treatment for the ovarian cancer.

5. The method of claim 1, wherein the subject exhibits an elevated serum level of one or more markers selected from the group consisting of CA-125, transferrin, transthyretin, apolipoprotein A1 (apoA1), beta-2 microglobulin (B2M), human epididymis protein 4 (HE4), human chorionic gonadotropin (HCG), alpha-fetoprotein (AFP), lactate dehydrogenase (LDH), inhibin, estrogen, and testosterone, relative to the serum level of the one or more markers in a subject not having ovarian cancer.

6. The method of claim 1, comprising administering to the subject four doses of the immunogenic composition, wherein each of the four doses comprises about 25 million of the mature cells.

7. The method of claim 6, further comprising administering to the subject two additional doses of the immunogenic composition, wherein each of the two additional doses comprises about 10 million of the mature cells.

8. The method of claim 1, wherein the ovarian cancer is a high grade serous ovarian cancer.

9. The method of claim 1, wherein the initial treatment comprises administering to the subject carboplatin and/or paclitaxel.

10. The method of claim 1, wherein the initial treatment comprises primary debulking surgery combined with adjuvant chemotherapy.

11. The method of claim 1, wherein the initial treatment comprises primary debulking surgery combined with six cycles of adjuvant chemotherapy.

12. The method of claim 1, wherein the initial treatment comprises neoadjuvant chemotherapy and interval debulking surgery.

13. The method of claim 12, wherein the initial treatment comprises three cycles of neoadjuvant chemotherapy and interval debulking surgery.

* * * * *